United States Patent [19]
Berger et al.

[11] Patent Number: 5,615,673
[45] Date of Patent: Apr. 1, 1997

[54] APPARATUS AND METHODS OF RAMAN SPECTROSCOPY FOR ANALYSIS OF BLOOD GASES AND ANALYTES

[75] Inventors: Andrew J. Berger; James F. Brennan, III, both of Cambridge; Ramanchandra R. Dasari, Lexington; Michael S. Feld, Newton; Irving Itzkan, Boston; Kaz Tanaka; Yang Wang, both of Somerville, all of Mass.

[73] Assignee: Massachusetts Institute of Technology, Cambridge, Mass.

[21] Appl. No.: 410,927

[22] Filed: Mar. 27, 1995

[51] Int. Cl.$^6$ .................................................. A61B 5/00
[52] U.S. Cl. .............................................. 128/633; 356/39
[58] Field of Search ................................ 128/633, 664, 128/665; 356/39, 301

[56] References Cited

U.S. PATENT DOCUMENTS

| | | | |
|---|---|---|---|
| 3,906,241 | 9/1975 | Thompson | 128/665 |
| 4,427,889 | 1/1984 | Müller | 128/633 |
| 4,648,714 | 3/1987 | Benner et al. | 128/633 |
| 5,011,284 | 4/1991 | Tedesco et al. | 356/301 |
| 5,106,387 | 4/1992 | Kittrell et al. | 606/15 |
| 5,194,913 | 3/1993 | Myrick et al. | 356/301 |
| 5,199,431 | 4/1993 | Kittrell et al. | 128/634 |
| 5,243,983 | 9/1993 | Tarr et al. | 128/633 |
| 5,261,410 | 11/1993 | Alfano et al. | 128/664 |
| 5,280,788 | 1/1994 | Janes et al. | 128/665 |
| 5,293,872 | 3/1994 | Alfano et al. | 128/664 |
| 5,372,135 | 12/1994 | Mendelson et al. | |

FOREIGN PATENT DOCUMENTS

| | | |
|---|---|---|
| 05256782 | 1/1994 | Japan. |
| 90/12536 | 11/1990 | WIPO. |
| 92/15008 | 9/1992 | WIPO. |
| 88/06726 | 9/1994 | WIPO. |

OTHER PUBLICATIONS

Berger, A.J., et al., "Rapid Noninvasive Concentration Measurements of Aqueous Biological Analytes by Near–Infrared Raman Spectroscopy," *Applied Optics* 35(1), 209–212 (1 Jan. 1996).

Tanaka, K., et al., "Compound Parabolic Concentrator Probe for Efficient Light Collection in Spectroscopy of Biological Tissue," *Applied Optics* 35(4), 758–763 (1 Feb. 1996).

Berger, A.J., et al., "Aqueous Dissolved Gas Measurements Using Near–Infrared Raman Spectroscopy," *Applied Spectroscopy* 49(8), 1164–1169 (1995).

Nie et al., "Applications of Near–Infrared Fourier Transform Raman Spectroscopy in Biology and Medicine," *Spectroscopy* 5(7):24–32 (no date given).

Ozaki, "Medical Application of Raman Spectroscopy", *Applied Spectroscopy Reviews* 24(3$4), 259–312 (1988).

Buontempo et al., "Spectroscopy with Nonimaging Optics: Application to the Infrared Spectroscopy of Langmiur Monolayers", *Applied Spectroscopy* 46(5):725–731 (1992).

Snail, "Reflector Design Using Nonimaging Optics", *Applied Optics*, 26(24):5326–5332) (15 Dec. 1987).

Snail et al., "Integrating Sphere Designs with Isotropic Throughout", *Applied Optics* 28(10):1793–1799 (15 May 1989).

(List continued on next page.)

Primary Examiner—Angela D. Sykes
Assistant Examiner—Eric F. Winokur
Attorney, Agent, or Firm—Hamilton, Brook, Smith & Reynolds, P.C.

[57] ABSTRACT

The present invention relates to systems of methods of measuring selected analytes in blood and tissue using Raman spectroscopy to aid in diagnosis. More particularly, Raman spectra are collected and analyzed to measure the concentration of dissolved gases and other analytes of interest in blood. Methods include in vivo transdermal and continuous monitoring as well as in vitro blood analysis.

38 Claims, 20 Drawing Sheets

OTHER PUBLICATIONS

Hanssen, "Effects of Restricting the Detector Field of View When Using Integrating Spheres", *Applied Optics* 28(11):2097–2103 (01 Jun. 1989).

DeBlase et al., "Infrared Emission Spectroscopy: A Theoretical and Experimental Review", *Applied Spectroscopy* 45(4):611–618 (1991).

Lewis et al., "Development of Near–Infrared Fourier Transform Raman Spectroscopy for the Study of Biologically Active Macromolecules", *Applied Spectroscopy* 42(7):1193–1188 (Sep./Oct. 1988).

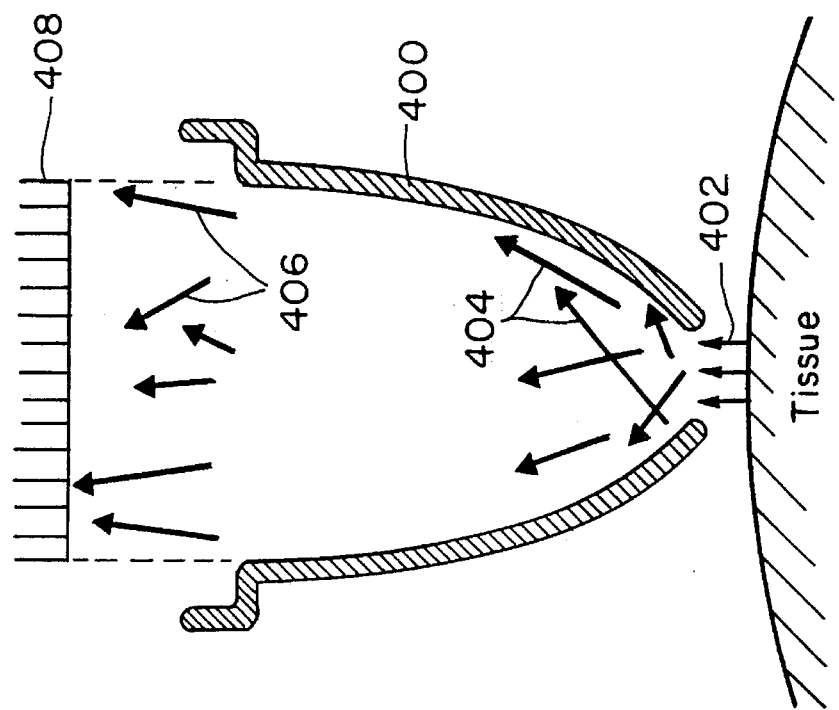
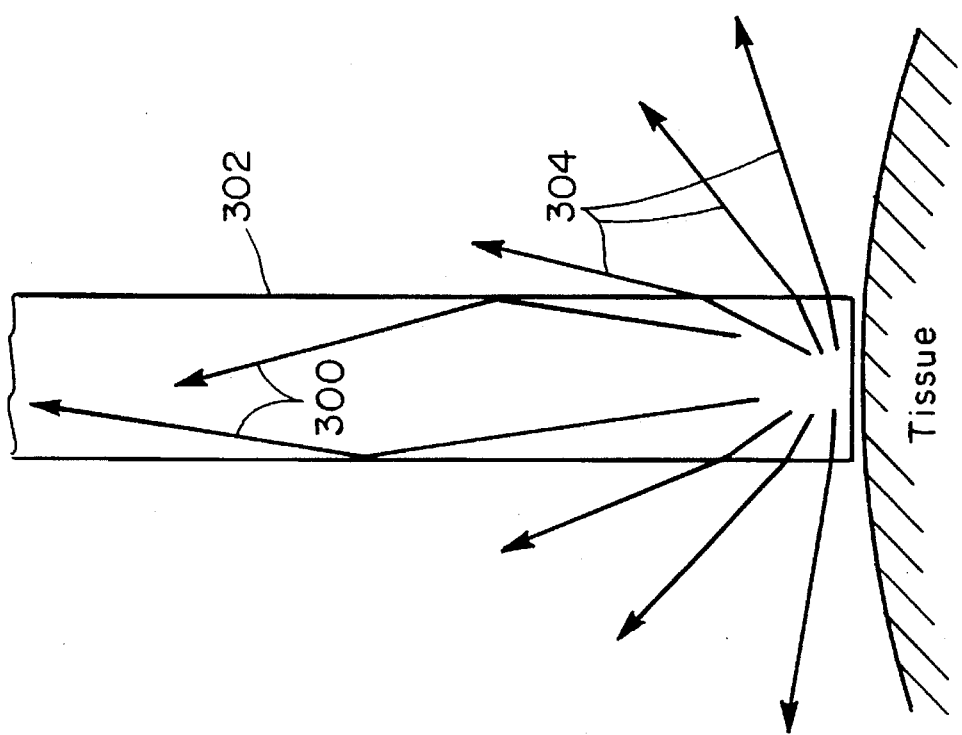
FIGURE 3A
FIGURE 3B

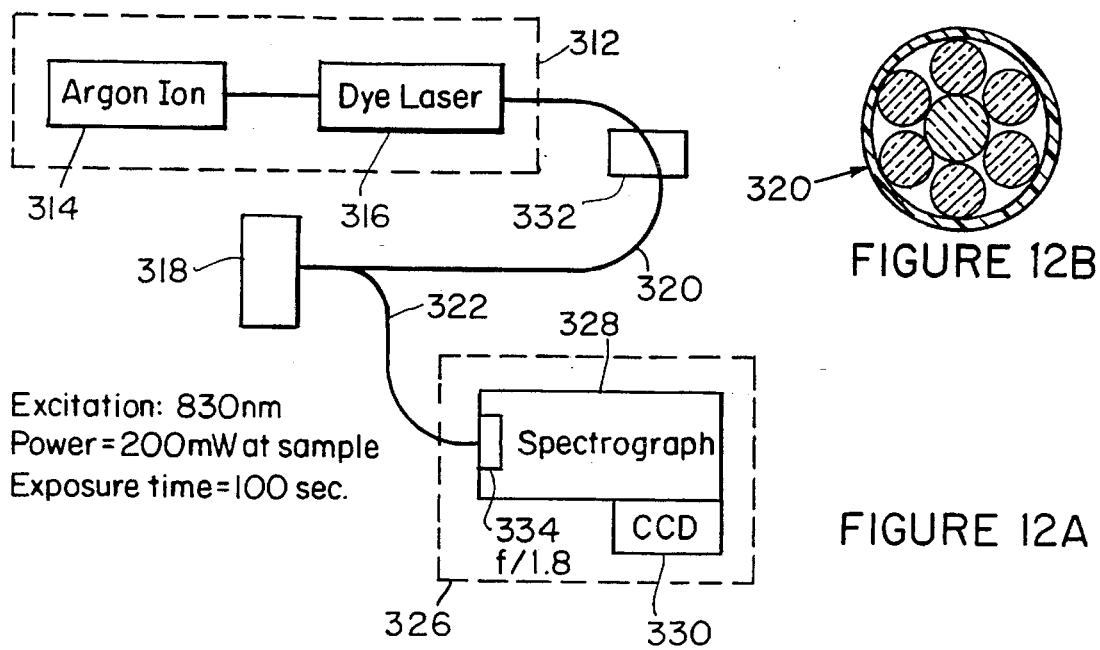
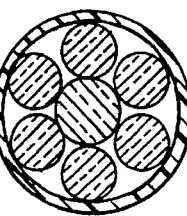
Excitation: 830nm
Power = 200mW at sample
Exposure time = 100 sec.
FIGURE 12B
FIGURE 12A
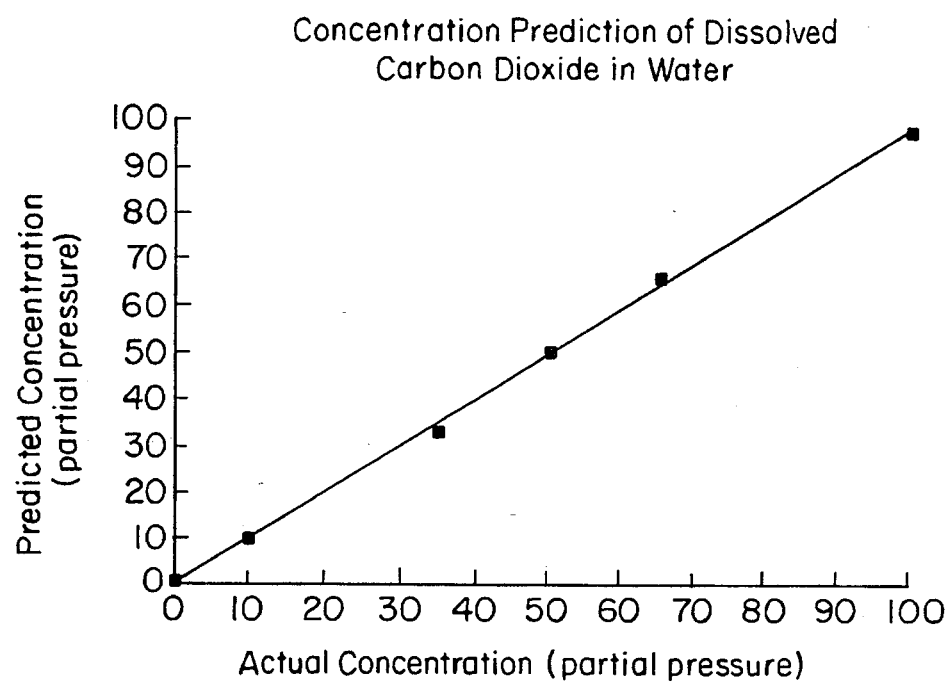
FIG. 11

APPARATUS AND METHODS OF RAMAN SPECTROSCOPY FOR ANALYSIS OF BLOOD GASES AND ANALYTES

BACKGROUND OF THE INVENTION

Information about the concentration of analytes in gases, liquids, and semisolid materials is required in many fields of science and technology, particularly in the field of medicine. The oxygen content of human blood, for example, provides important clinical information for the treatment of certain conditions and diseases. Although pulse oximeters can provide non-invasive measurement of the extent of oxygen saturation in hemoglobin, they do not give information on the concentration of dissolved oxygen in blood.

For quite some time the state-of the art for measuring oxygen concentration in blood has been the electrode probe based on the reduction of molecular oxygen. Certain electrochemical oxygen sensors, both polarographic and galvanic, have been applied with success to both aqueous and nonaqueous solutions in which oxygen is simply dissolved without the possibility of reaction, and to those in which oxygen can react reversibly, as in blood. There are, however, several drawbacks associated with this technique. Patients undergoing blood gas analysis are subjected to the procedure of withdrawing blood from an artery. The method also lacks the capability for continuous in-situ monitoring.

In current commercial systems, the average turn-around time is on the order of half an hour. In addition, risks exist for infection, contamination, and exposure to viruses during the transferring and handling of blood. A need exists for improved systems and methods which provide more complete and accurate information with respect to blood gases and other analytes and which reduces the associated risks to the patient and the providers of health care.

SUMMARY OF THE INVENTION

The present invention relates to optical systems and methods employing Raman spectroscopy for the analysis of blood gases and other analytes. Unlike fluorescence based methods, Raman spectroscopic methods of the present invention provide extensive molecular level information about dissolved human blood gases such as oxygen and carbon dioxide, as well as other analytes. Raman spectroscopy has previously been used to measure calcified plaque in bulk that has been deposited on artery wall, for example. Raman spectroscopy has not been used to measure in vivo blood metabolic processes. These metabolic processes can include the measurement of diffusion of various blood analytes into tissue. Other analytes including electrolytes containing sodium, potassium, and calcium, can also be measured in conjunction with the methods and systems described herein. The methods can include transdermal measurements through the human skin using fiber optic probes. In particular, a preferred embodiment utilizes Raman spectra of these gases for determining their concentration levels in blood. Further, in situ vibrational spectroscopic methods allow continuous monitoring of human blood for measuring molecular level changes in dissolved gases and analytes.

These methods include the steps of irradiating the blood region to be analyzed below a portion of tissue with laser radiation in the near-infrared range of the electromagnetic spectrum, detecting Raman-scattered light from the blood region in response to the laser radiation, and analyzing the detected light to determine concentrations of one or more dissolved gases. The methods further include using a fiber optic device for transmitting excitation radiation and/or collecting the frequency-shifted Raman response signal returning from tissue.

The use of Raman spectroscopy is well suited for blood analysis, more particularly, near-infrared (NIR) Raman spectroscopy provides the advantages of: (1) minimal water interference, (2) compatibility with optical fiber technology, and (3) ability to penetrate deeply into tissue and to probe sub-surface features. However, up to now, NIR Raman spectroscopy has not been a realistic option for analysis of dissolved gases, due to weak intensities compared to those of fluorescence (typically one million times smaller) the small concentration levels of many analytes of interest and the difficulty of performing non-invasive measurements through the skin.

A preferred embodiment of the present invention features a charge-coupled-device. (CCD) based detector system to greatly enhance detection resolution and to overcome previous limitations over Raman signal detection. Such devices compliment NIR Raman spectroscopy by providing excellent sensitivity in the near-infrared region and extremely low level of background and readout noise. Additionally, as part of such a detector system, the preferred embodiment features an improved spectrograph which is constructed based on a transmission volume holographic grating. The detection system comprising the spectrograph coupled to a CCD is well suited for studying biological samples and tissue where endogenous fluorescence can interfere with Raman measurements.

Tradeoffs between CCD sensitivity and the amount of tissue fluorescence indicate that a preferred spectral window for NIR Raman spectroscopy is in the region of 700 to 1300 nm, and preferably between 800 and 1000 nm. A particular embodiment of the present invention features a tunable diode laser source to provide excitation light in this preferred range.

Yet another preferred embodiment of the present invention employs an optical collimator to maximize collection of Raman-scattered signal over a range of incident angles. In particular, a preferred embodiment having a compound parabolic concentrator (CPC) that is optically coupled to a high resolution detection system results in an improved signal to noise ratio. In this embodiment, light emitted by an excitation laser is carried by an optical fiber. Prior to irradiating a region of interest (e.g., a volume of blood below skin tissue), the laser radiation is filtered to remove any background light generated by the optical fiber carrier. In response to irradiating the selected volume with the filtered excitation laser, Raman signals are produced and collected. In this embodiment, the CPC is aligned on top of the surface area above the target volume to collect and collimate scattered Raman signals. The CPC provides a significantly improved angle of acceptance to collect Raman shifted rays up to approximately 16 degrees from the test-surface horizontal. Thus, the CPC is not used in its traditional function of concentrating light incident on the large aperture end, but in its collection function, is used to collimate light collected at its small aperture end. Raman signals received by the CPC can also be filtered to remove background light. Raman signals are then collected by a high capacity collection fiber bundle which is coupled to a detection system comprising a spectrograph and a charge-coupled-device.

In other embodiments, other collection systems can be used with or without holographic filters at the distal end of the probe. Holographic filters can enhance both delivery and collection efficiency if certain well defined wavelengths are needed to optimize measurement of certain analytes. Interference filters can also be used to perform measurements of selected wavelengths without a spectrograph. These systems can be used as a hand held probe to provide non-invasive transcutaneous measurements.

There are particular dissolved blood gases of interest, including $O_2$ which has a strong Raman band at 1556 cm$^{-1}$, and $CO_2$ which has two Raman bands at 1286 and 1388 cm$^{-1}$. Also, there is a large $H_2O$ background peak in this region. Given the known spectroscopic parameters, the Raman spectroscopic methods of present invention can accurately determine physiological concentrations of these gases in aqueous solutions such as whole blood, or other solutions containing blood components, by collecting Raman spectra of these gases, and then subtracting the background spectrum. Other dissolved gases that can be measured by the systems described herein including NO. Blood analytes of diagnostic interest which are measured by the systems described herein include glucose, lactic acid, creatinine, bicarbonate and electrolytes.

Additionally, preferred embodiments of the invention utilize analytical procedures to provide improved measurements of blood analyte concentration. These can selectively include subtraction of any background spectral components, deconvolution methods, partial least squares methods and comparison of measured spectra with Raman spectral reference data that has been stored in computer memory.

The above and other features of the invention including various novel details of construction and combinations of parts will now be more particularly described with reference to the accompanying drawings and pointed out in the claims. It will be understood that the particular system and methods embodying the invention are shown by way of illustration only and not as a limitation of the invention. The principles and features of this invention may be employed in varied and numerous embodiments without departing from the scope of the invention.

BRIEF DESCRIPTION OF THE DRAWINGS

FIG. 3A is shows a fiber bundle and the rays emanating from a sample surface indicating that conventional fiber optics have a lower acceptance angle for collecting returning scattered light.

FIG. 3B shows the basic configuration of a compound parabolic concentrator (CPC).

FIG. 11 graphically illustrates partial-least square analysis of the data presented in FIGS. 10A and 10B; the solid line represents the prediction and the stars represent the actual data points.

FIG. 12A shows another embodiment of Raman spectroscopy system of the present invention used for measuring blood analytes.

FIG. 12B is a cross-sectional view of the fiber optic cable in FIG. 12A.

DETAILED DESCRIPTION OF THE INVENTION

The present invention is directed to systems and methods for measuring concentration of dissolved gases and analytes in human blood.

Near-infrared (NIR) Raman spectroscopy systems and methods of the present invention provide techniques for analyzing biological substances. In particular, light in the near-infrared is non-mutagenic and has a relatively large penetration depth (>1 mm) into tissue in the wavelength range between 700 and 1300 nm, allowing non-invasive, non-destructive analysis of bulk samples in vivo. Raman spectroscopy offers many advantages over absorption/reflectance methods as a diagnostic technique in this wavelength range. NIR Raman spectra of biological materials contain sharp peaks, corresponding to fundamental modes of vibration, whereas the overtone and combination absorption bands in the NIR are broad. As such, Raman spectroscopy has an inherent advantage in mixture analysis since the spectral similarity between signals from different species is much less severe. Also, with the use of the systems of the present invention, Raman signals can be detected using a back-scattering geometry. This makes it possible to probe the upper layer of samples which are too thick for transmission measurements.

By measuring the Raman spectra of gases reference spectra can be prepared for use in connection with the analysis of dissolved gases in blood. For example, $O_2$ has a strong Raman band at 1556 cm$^{-1}$, and $CO_2$ has two Raman bands at 1286 and 1388 cm$^{-1}$. Also, there is a large $H_2O$ background peak in this region. Given the known spectroscopic parameters, the Raman spectroscopic methods of the present invention can accurately determine physiological concentrations of these and other gases in aqueous solutions. By comparing Raman spectra from selected sample gases to reference background spectra as well as the spectra of saturated aqueous solutions, and analyzing the measured spectra such as by subtracting the appropriate background spectrum, the concentration level of selected tissue and blood analytes can be determined. For example, in one particular embodiment, $2.2 \times 10^{-3}$ moles/liter of dissolved oxygen was measured in the presence of 55 moles/liter of water. The concentration of oxygen was determined to be $2.2 \times 10^{-3}/55 = 4.4 \times 10^{-3}$, or 44 ppm (parts per million) of the solution.

Figure 1:
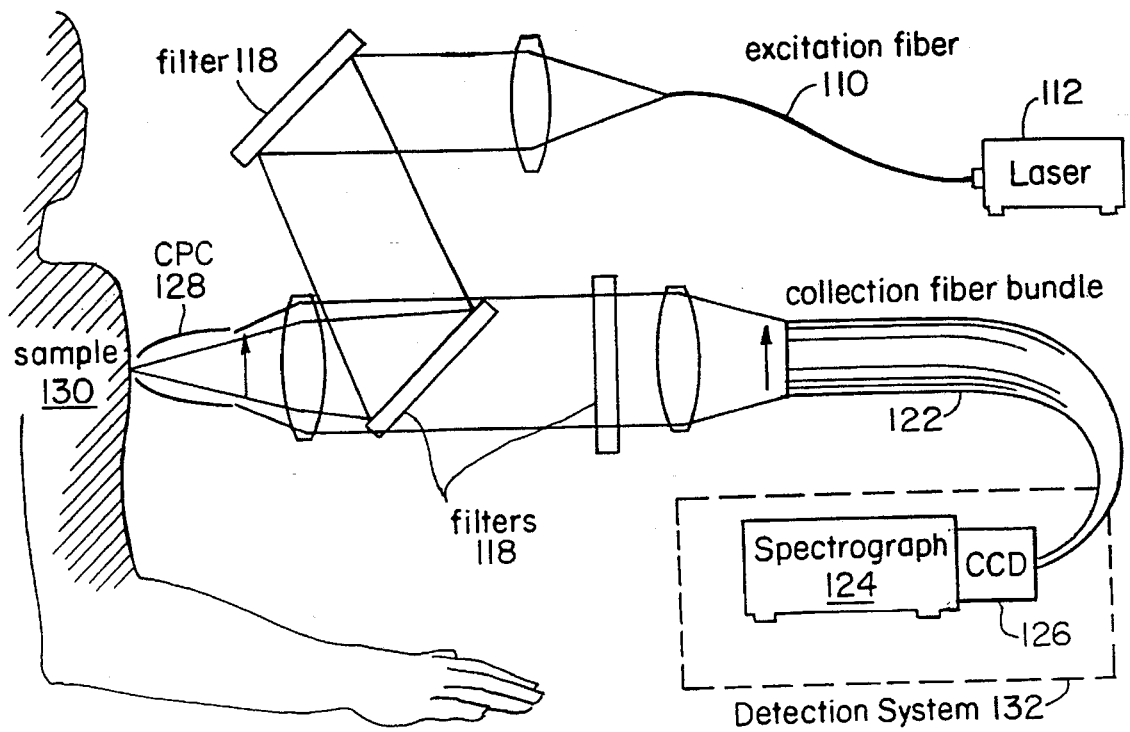
FIG. 1 is a schematic diagram of a Raman spectroscopy system used for in vivo and/or in vitro analysis of blood constituents in accordance with the present invention.

Referring now to the drawings, FIG. 1 is a schematic diagram of a Raman spectroscopy system which can be used to perform the methods of the present invention. Methods for performing Raman spectroscopy for diagnosis and treatment of tissue are described in two applications by Joseph Baraga et al. filed on Aug. 25, 1993 and Aug. 11, 1994, which correspond to U.S. Ser. Nos. 08/107,854 and 08/288,990, respectively, both of which are incorporated herein by reference. Systems described in the above referenced applications can be used with the methods and systems described herein to provide a catheter system for invasive monitoring of analytes suspended or dissolved in blood. The laser excitation source 112 for this particular Raman spectroscopy system is a tunable diode laser set to 830 nm, with line width <10 GHz, and typically powered at about 200 mW. Depending on the sensitivity of the detection system in use and the amount of fluorescence emitted by the sample media being analyzed, the optimal laser excitation range is between 800 and 1000 nm. The choice of 830 nm near infrared excitation wavelength reduces sample fluorescence without unduly compromising the detector sensitivity. Light from the laser is then coupled into a 50 micron diameter optical fiber 110. Dichroic beamsplitters or, in this embodiment, three holographic filters 118, are used to image the excitation light at the output of the optical fiber 1:1 onto a region or sample 130 of interest. The output face of this excitation fiber is imaged onto the sample, producing a 50 micron illumination spot. In this embodiment a compound parabolic concentrator (CPC) 128 can optically be used to collect the Raman scattered light returning from the region of interest including Raman scattered light shifted by dissolved gases and other analytes contained in the blood underlying the dermal tissue. The dichroic beamsplitter images the CPC output 1:1 directly onto a collection optical fiber bundle 122.

To minimize the amount of optical fiber generated background light from entering the spectrograph 124, the excitation and collection fibers are filtered. The excitation laser radiation, after delivery to the region of interest, scatters back and tends to enter collection fiber along with Raman scattered radiation, the former causing significant fiber background noise. In this preferred embodiment, holographic notch filters are used which provide optical density of 4 or more at the excitation wavelength and transmit 80% of the Raman scattered light. In this manner, the Raman spectrum of the silica in the excitation fiber is filtered out at the first mirror, and most of the laser light or other light reflected by the tissue is prevented from entering the collection fiber.

Figure 2:
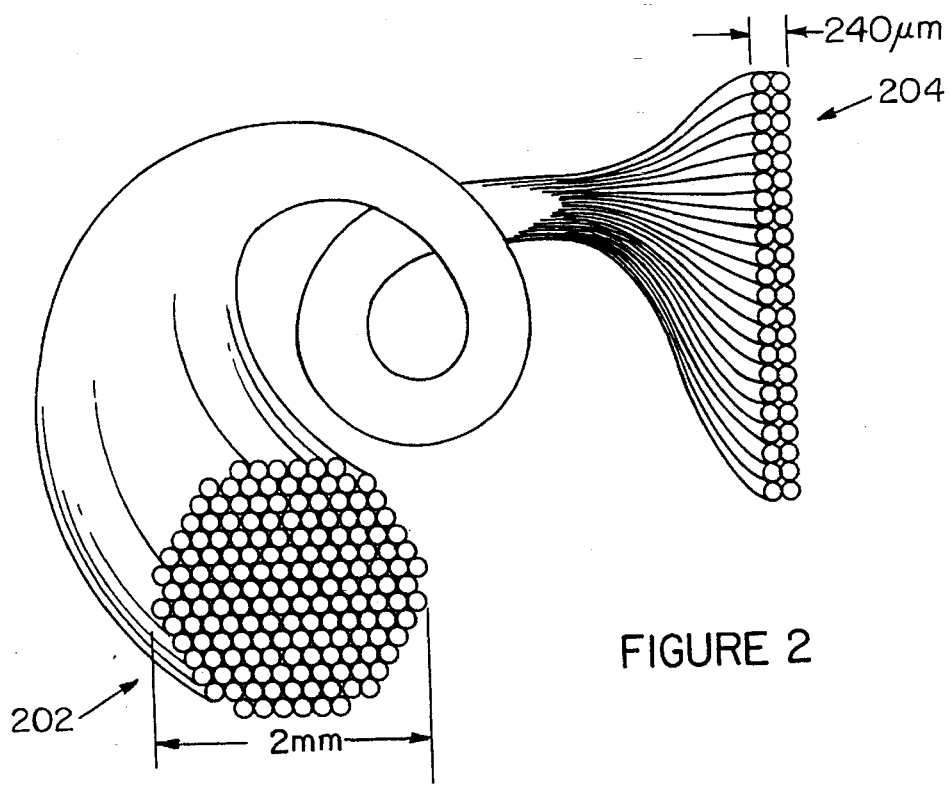
FIG. 2 is an enlarged view of the collection fiber bundle of the Raman spectroscopy system in FIG. 1.

The collection fiber or bundle 122 comprises 200 fibers having numerical aperture of 0.29 with inner core of 100 μm diameter and a cladding diameter of 140 μm. As shown in FIG. 2, at the receiving or distal end 202, the fibers are grouped into a circle of 2 mm diameter which matches the CPC output dimension. The proximal end 204 of the fiber bundle is arranged to interface the input end of the detection system. In this embodiment, the fibers are arranged in 2 columns of 100 fibers to define a slit width of 240 μm (see FIG. 2). Light from the collection fiber is then channeled to a HoloSpec f/1.8 Kaiser spectrograph 124 with a linear dispersion of 3.4 nm/mm. The spectrograph disperses the light onto a back-illuminated, thinned Tektronix charge coupled device (CCD) 126 with 512 by 512 pixels, that is cooled by liquid nitrogen and is controlled by a Princeton Instruments driver. Other available CCDs, such a deep-depletion CCD, can also be used.

A problem commonly encountered in spectroscopy is the collection of weak signals from scattering media, such as fluorescence and especially Raman, which are often inadequate for measurement purposes. In order to increase the signal to noise ratio, it is advantageous to collect as much of the Raman signal as possible. As shown in FIG. 3A, conventional optics 302 provide rather limited collection system. Here, a relatively small portion 300 of the scattered light, having near vertical reflection angle, is collected into the optical fiber. Optical fibers used for remote collection in spectroscopy, having a limited acceptance angle, fail to collect a portion of the scattered light 304 that is widely dispersed from the sample as shown in FIG. 3A. A compound parabolic concentrator (CPC) (see FIG. 1, element 128) is a non-imaging optical element used to convert light radiated over a full hemisphere into a narrow cone which can be collected by conventional optics, including optical fibers and lenses. The basic configuration of a CPC is shown in FIG. 3B. Note that the angular orientation of the CPC as shown FIG. 3B enables much of the widely scattered light, such as Raman, spanning up to about 16.2 degrees from the surface horizontal, to be collected from the sample surface. Here, the input light 402 (e.g. Scattered Raman) is distributed over $2\pi$ steradian. Approximately 96% of the output light 406 will be within the acceptance angle of an optical fiber bundle 408. In a preferred embodiment, a CPC can be implemented as shown in FIG. 1. In FIG. 1, the input (collection) end of a CPC 128 makes contact with the sample while the output (wider) end is coupled to the input end of the collection fiber optic bundle 122 through the holographic dichroic beamsplitter 118.

Figure 3C:
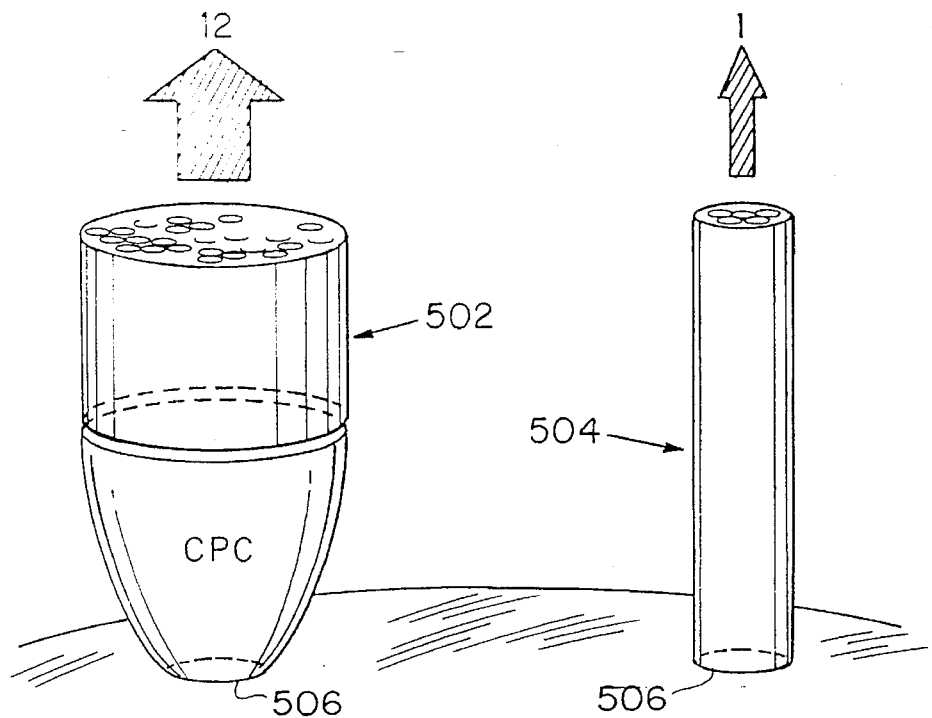
FIG. 3C shows an example of a CPC (a) made to be coupled directly to a fiber optic bundle, and a fiber bundle (b) having an equivalent input aperture.

In a particular embodiment, the dimensions of a CPC were made so that it could match the collection ability of a given spectroscopic system having, at its input end, an optical carrier to transmit the collected light. Hence, the CPC dimensions are defined by the f-number and slit width of a particular optical carrier. The shape of a particular CPC is uniquely defined by giving its entrance dimension and numerical aperture into which the light must be transformed. FIG. 3C shows an example of a CPC 502 made to be coupled directly to a fiber optic bundle of certain dimensions. Note that, by comparison, a single fiber bundle 504 of an equivalent input aperture 506 transmits an arbitrary output of 1 whereas the CPC coupled bundle can transmit an output of 12.

Figure 4A:
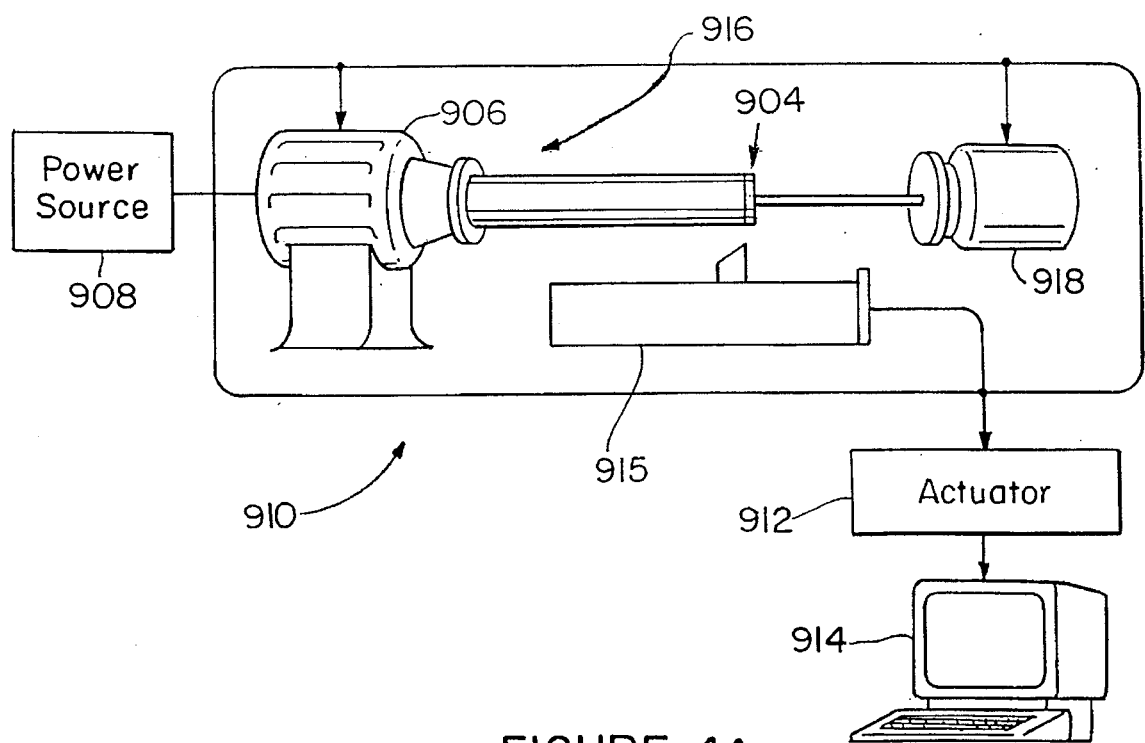
FIG. 4A shows an apparatus for forming a parabolic tip on one end of a mandrel.
Figure 4B:
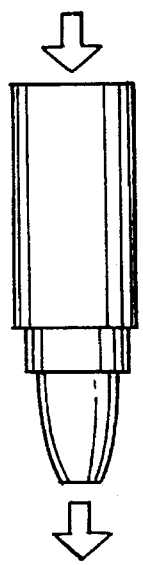
FIG. 4B is a preformed mandrel having a parabolic tip formed by the method described in FIG. 4A.

Commercially available CPC's are too large to launch into contemporary spectrometers. In one embodiment of the present invention, a miniature CPC, as required for a Raman system, was fabricated. As shown in FIGS. 4A–4D a preferred method of manufacturing such a miniature CPC can include a computer controlled lathe 910 that is used to form a parabolic tip on one end of a mandrel which followed the CPC cross-section function as follows:

$$r^2C^2 + r[2SCz + 2a'(1+S)^2] + [z^2S^2 - 2a'C(2+a'^2(1+S)(3+S)] = 0 \quad (1)$$

where z is the distance along the mandrel axis, and r is the radius of the mandrel at a given point along the axis z, a' is the radius of the sample collection area, $C = \cos f$, where f is the maximum fiber acceptance angle, and $S = \sin f$. Referring back to FIG. 4A, a pre-cut mandrel 904 is suspended in a metal-forming apparatus 916. One end of the mandrel is coupled to a motor head 906, and the opposite end is coupled to a suspender 918. As the mandrel is rotated by the motor, the lathe shaves one end of the mandrel according to a set of angular displacement instructions provided by a computer 914. The computer generates a set of displacement instructions corresponding to equation (1). A set of electrical signals corresponding to such instructions are then fed into an actuator 912 which maneuvers the lathe according to the displacement instructions. FIG. 4B is a preformed mandrel with a parabolic end 808 as fabricated according to the method described in FIG. 4A.

Figure 4C:
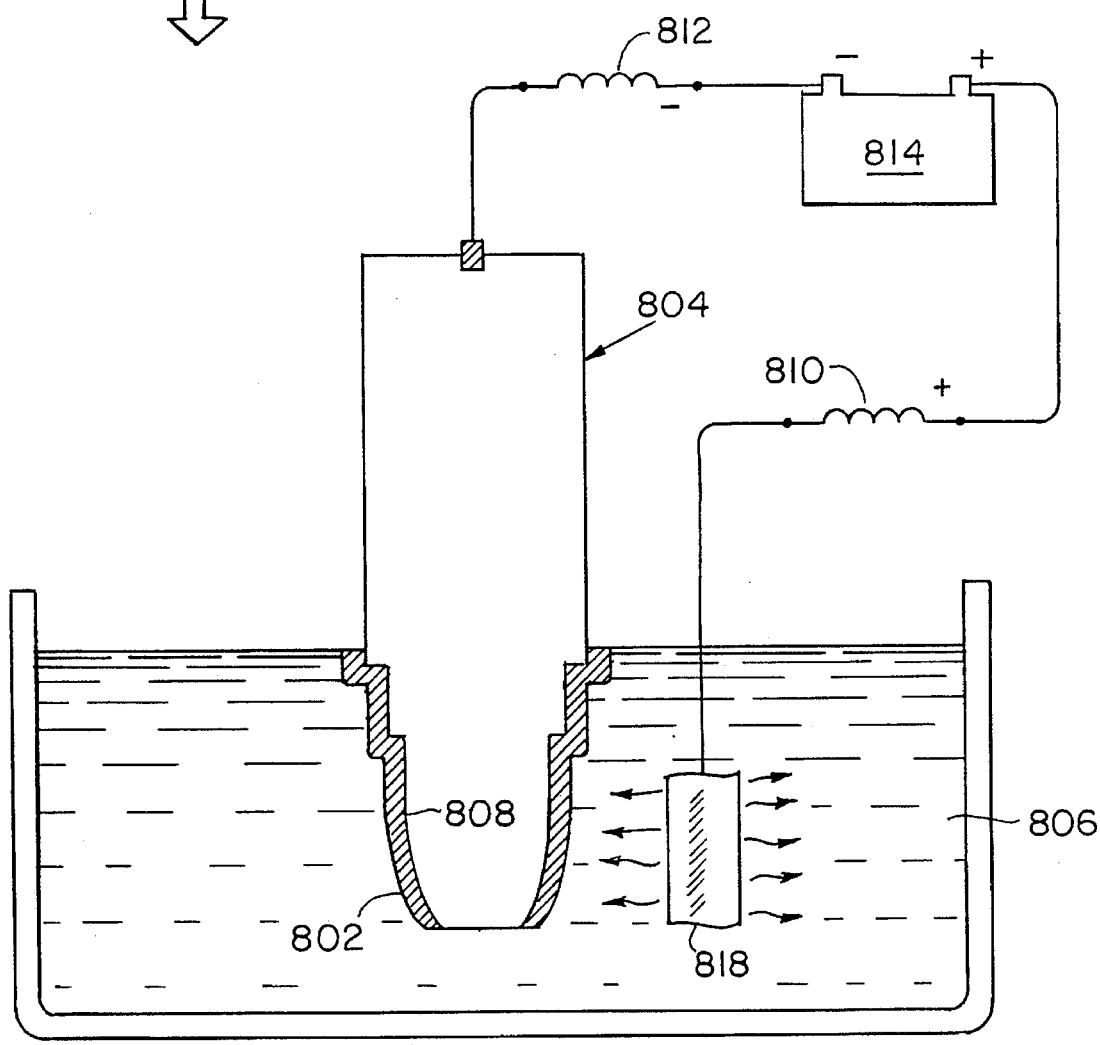
FIG. 4C illustrates a process for fabricating a miniature CPC by electroforming.

FIG. 4C illustrates a CPC fabrication process involving electroforming. In FIG. 4C, a preformed mandrel 804 according to the method illustrated in FIG. 4A is immersed in a bath of electrolyte 806. In the same electrolyte bath, a piece of nickel plate electrode 818 is also immersed. The negative pole 812 of a direct current source 814 is coupled to the preformed mandrel forming cathode, and the positive pole 810 of the current source is coupled to the nickel electrode forming anode. The nickel is then electrolytically deposited along the wall of the preformed mandrel tip 808 and forms a nickel shell 802 of certain thickness. The process of electroforming is terminated when a desired thickness of nickel has been deposited on the mandrel. The mandrel having nickel coated at the preformed end is then removed, producing a hollow nickel shell. The shell is then made into a CPC by optically coating the interior wall of the shell (see FIG. 4D).

Figure 4D:
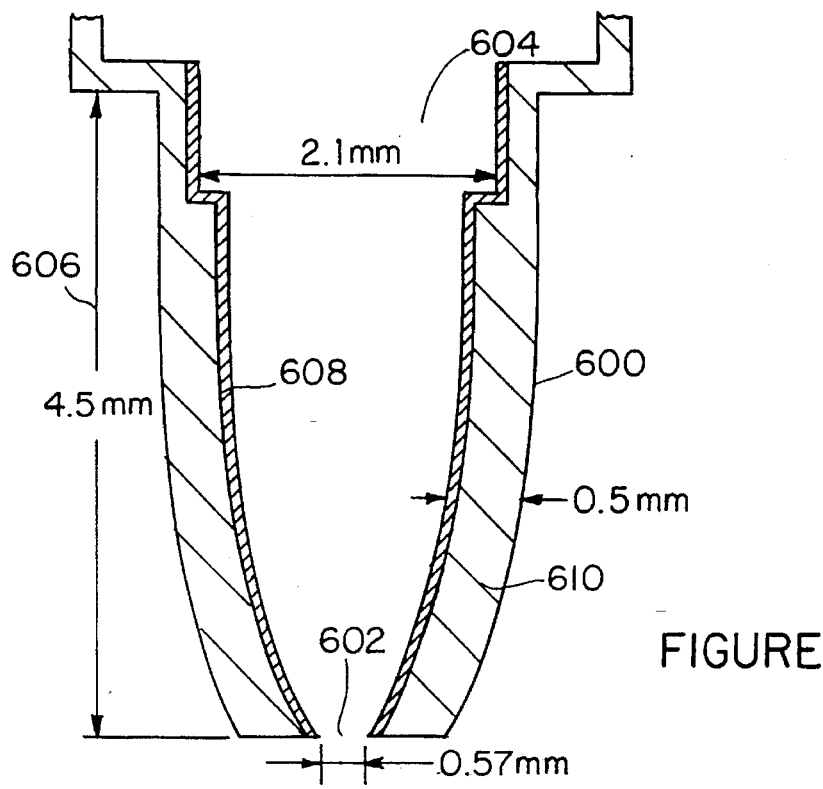
FIG. 4D illustrates specific dimensions of a particular CPC fabricated by the methods described in FIGS. 4A through 4B.

The final dimensions of such CPC are shown in FIG. 4D, where the finished CPC 600 had an input diameter 602 of 0.57 mm, an output diameter 604 of 2.1 mm, and a total length 606 of 4.5 mm. The thickness 610 of the main wall is 0.5 mm. For near infrared Raman spectroscopy, a layer 608 of the interior wall of the nickel CPC is coated with a highly reflective metal such as gold.

Figure 5A:
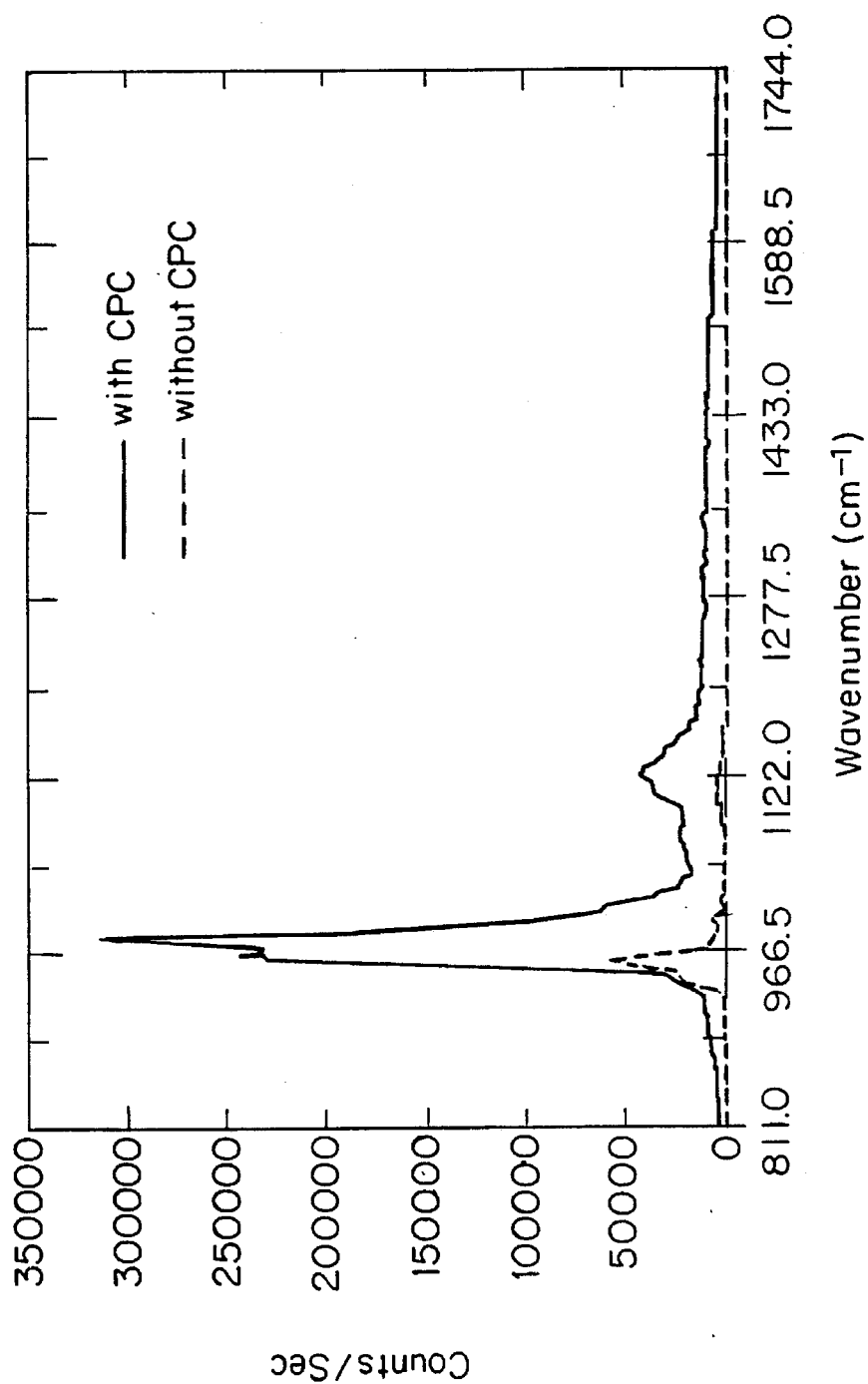
FIG. 5A graphically illustrates a comparison of the Raman spectra of $BaSO_4$ measured with and without the use of CPC in a Raman spectroscopy system.

FIG. 5A illustrates the effectiveness of the CPC for use in a system involving collection of Raman spectra. Here, $BASO_4$ Raman spectra was first collected with a CPC-filter system as shown in FIG. 1 and then with a conventional fiber optic probe having the same dimensions of the CPC input aperture. The two measurements were made on the same spot of the sample so as to avoid effects of sample inhomogeneity. The laser power used on the sample was 200 mW. FIG. 5A graphically illustrates the spectra collected over 0.25 seconds. Integrating the main peak and subtracting the bases showed that the CPC in this particular embodiment collected 7.5 times more light than without it.

Figure 5B:
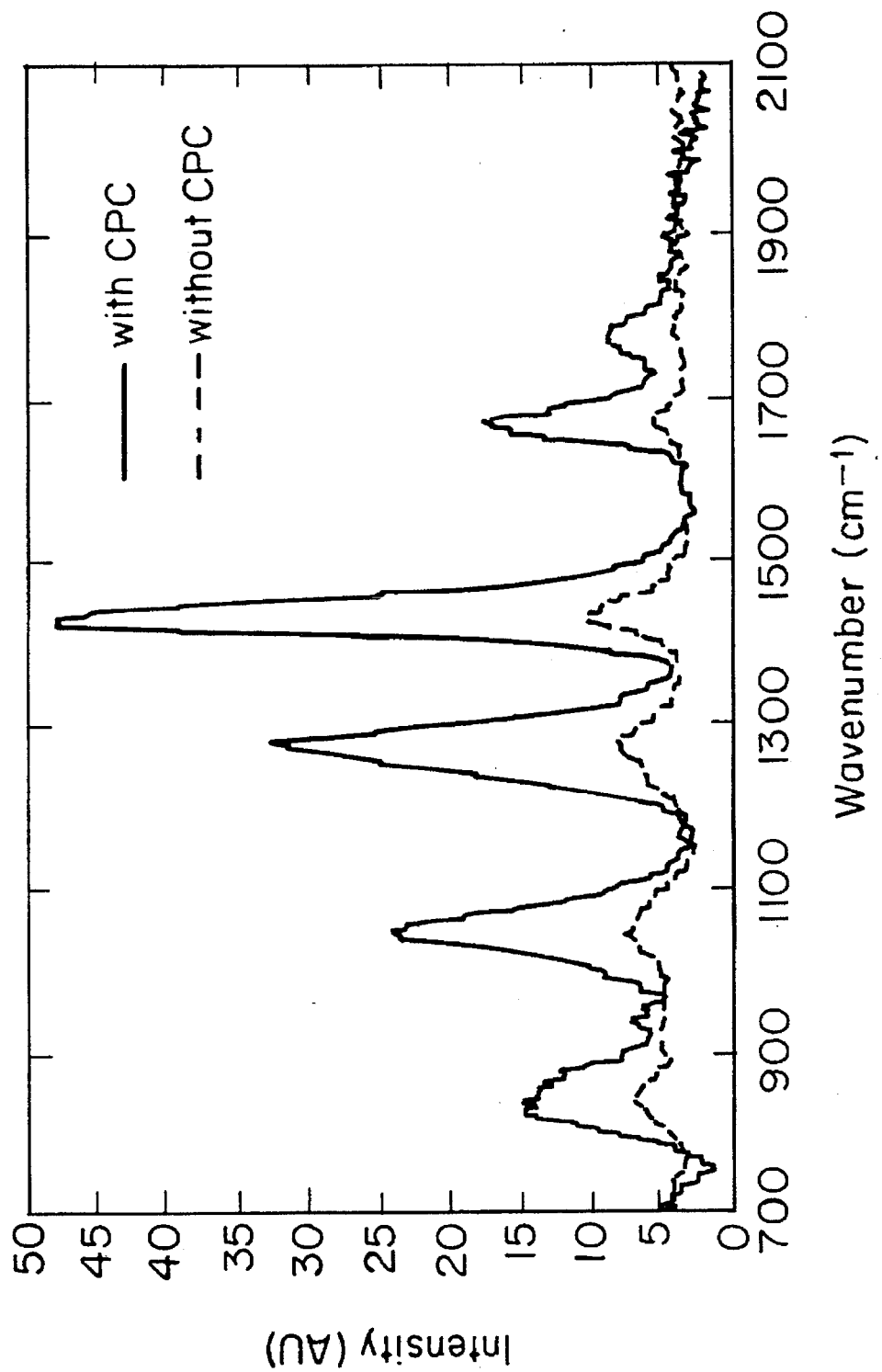
FIG. 5 graphically illustrates Raman spectra analysis of human breast tissue with and without a CPC-based collection method.

In another application of a Raman spectroscopy system, a CPC can be used to efficiently collect high level of Raman signals from bulk biological tissue. FIG. 5B graphically illustrates that the CPC-based collection method as described above improved the amount of collected light relative to a non-CPC method by a factor of 5. In this measurement, normal human breast tissue was chosen. Samples were obtained at the time of postmortem biopsy examination rinsed with isotonic saline solution buffered at Ph 7.4, snap-frozen in liquid nitrogen, and stored at −85 degrees Celsius until use. Prior to spectroscopic analysis, samples were passively warmed to room temperature while being kept moist with isotonic saline. Normal breast tissue was identified by gross inspection, separated, and sliced into roughly $4 \times 4$ mm$^2$ pieces. The tissue samples were placed in a metal cell with an open window with a small amount of isotonic saline to keep the tissue moist, and the surface that was placed in contact with the CPC entrance was irradiated by the laser. After spectroscopic examination, all specimens were histologically analyzed to verify the gross identifications. The spectra were collected over 10 seconds. Shorter or longer collection times can be used for in vivo and in vitro measurements depending upon the particular application. The collected spectra were white-light calibrated and the tissue fluorescence subtracted by using a polynomial fit. The CPC can be used for spectroscopic measurements of biological fluids as well as both thin and thick tissue regions of interest and is thus of general in vivo use for a wide variety of spectroscopic and particularly for diagnostic applications including cancer and pre-cancerous lesions.

Figure 6:
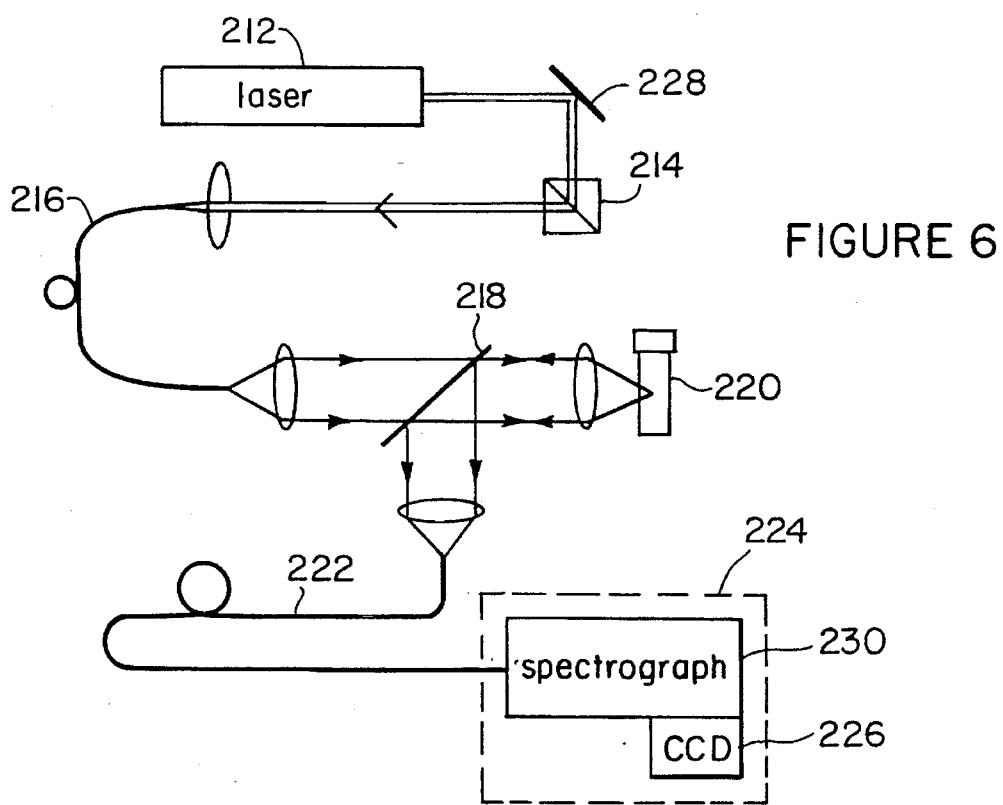
FIG. 6 is yet another embodiment of a Raman system of the present invention.

In another preferred embodiment as shown in FIG. 6, the laser source 212 for a Raman spectroscopy system is again a tunable diode laser set to 830 nm. Again, this choice of wavelength reduces sample fluorescence without unduly compromising the CCD detector 226 sensitivity. In addition, near infrared light is useful for non-invasive medical applications because it penetrates significantly (>1 mm) into tissue, making it possible to probe beneath the surface of skin. An excitation light 228 from this laser is holographically bandpass-filtered by a Kaiser notch filter 214 and coupled into a 50 micron diameter excitation optical fiber 216. A dichroic beamsplitter 218 then images the laser at the excitation fiber output 1:1 onto a sample 220, and then images the Raman signal emerging from the sample surface 1:1 onto a collection fiber 222 of diameter 100 microns and numerical aperture 0.29. Laser power at the sample is typically 200 Mw. The Raman scattered light from the collection fiber is then coupled directly into a detector system 230 consisting of a single-stage f/1.8 spectrograph 224 (Kaiser) coupled to a transmissive holographic grating and a back-thinned, 512—by—512 element CCD detector 226 (Tektronix, Princeton Instruments). The CCD can be binned vertically to produce a single 512-pixel spectrum and/or used for normal or spectroscopically enhanced imaging of tissue.

FIGS. 7A to 7E show the background subtracted spectra for a set of dissolved gases and corresponding gaseous phase spectra as measured by the system shown in FIG. 6. Here, the dissolved gas samples were prepared by bubbling the gas directly into a small volume (4 ml) of phosphate-buffered saline (PBS) in a glass screw-top bottle. After at least five minutes of vigorous bubbling to ensure saturation, the bottles were quickly capped and sealed. As a test of reproducibility, duplicate samples were prepared. Gaseous samples were prepared by flowing gas at a similar rate into an empty bottle for at least 30 seconds and then capping. Duplicates were again prepared.

The method of gathering Raman spectra in this particular embodiment (shown in FIG. 6) is non-invasive, sealed sample bottles are simply placed in the laser path. Wavenumber calibration of the spectra was performed using neon emission lines and indent as a Raman standard. The spectral resolution of the system, as measured on the neon lines, was found to be about 13 $cm^{-1}$, determined mainly by the diameter of the optical fiber. Spectra of the samples were gathered typically for one minute. For purposes of background subtraction, spectra of pure PBS and of room air were gathered at the same time as the dissolved and gaseous spectra, respectively. In the case of $O_2$ measurements, nitrogen was used to flush $O_2$ from the background.

In order to compare dissolved and gaseous cross sections and to compare signals from different gas species, correction factors are used to interpret the spectral data. To correct for the nonuniform spectral response of the spectrograph/CCD system, spectra are divided by a spectrum of white light. Subtraction of the background spectrum is accomplished either directly or, for extra precision, by a least-squares fit. Following such background subtraction, the Raman signal is measured by integrating the area underneath the peak and subtracting the area underneath the baseline. Each of the measurements shown in FIGS. 6A through 6E was checked with a corresponding scan of the duplicate sample. In all cases, the areas determined for these samples matched to within 5%. The area under the $H_2O$ band at 1640 $cm^{-1}$ was also calculated as an internal standard for the throughput of the collection system. Comparison with pure PBS spectra showed that the presence of dissolved gas had a negligible effect upon the strength of the $H_2O$ signal.

An additional correction factor is typically required in the data analysis to account for the different refractive indexes of air and water. This difference causes a small change in the efficiency of the excitation-collection geometry. In the present embodiment (see FIG. 6), in which a small diameter collection fiber is imaged onto the front of a relatively large cuvette and the excitation region is narrow, it can be shown that the Raman signal is collected approximately n times more efficiently in air than in water, where n is the refractive index of water. Since the refractive index of water at room temperature is 1.33, the gaseous phase Raman signal is collected 33% more efficiently than the dissolved gas signal.

Figure 7A:
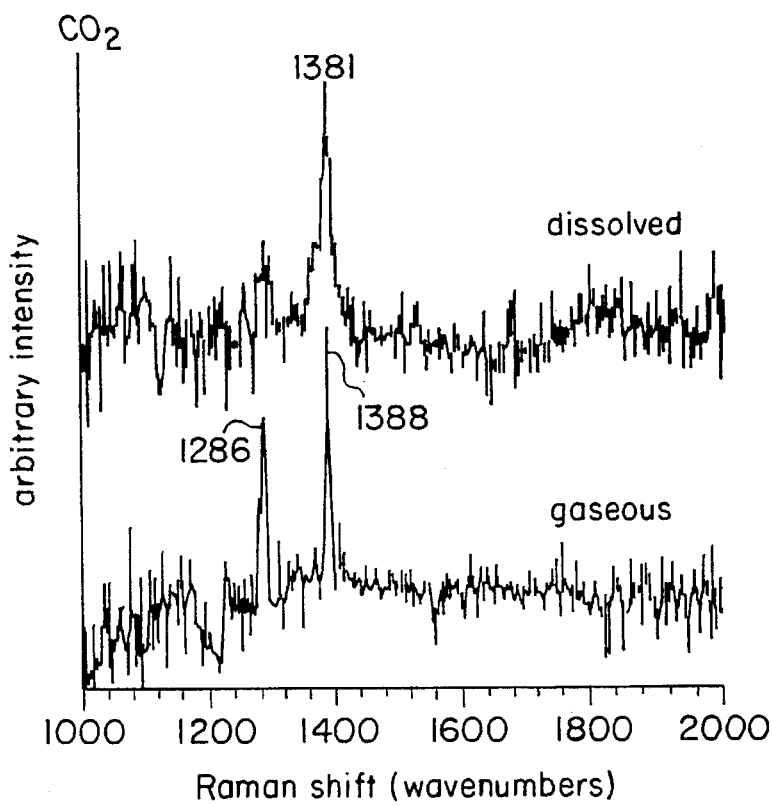
FIG. 7A graphically illustrates Raman background subtracted spectra of dissolved and gaseous $CO_2$ taken at 60 second integration.
Figure 7B:
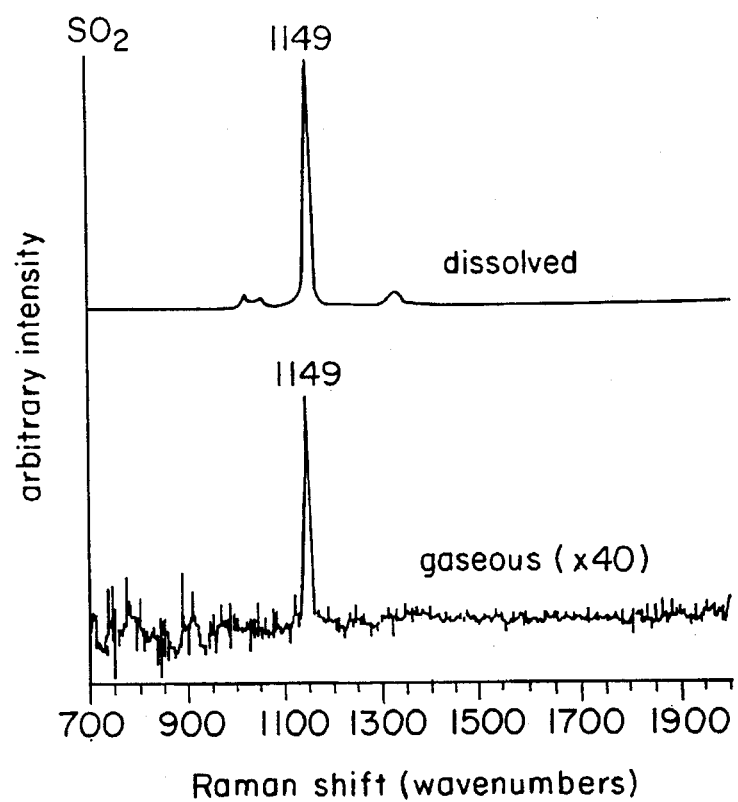
FIG. 7B graphically illustrates Raman background subtracted spectra of dissolved and gaseous $SO_2$ taken at 60 second integration.
Figure 7C:
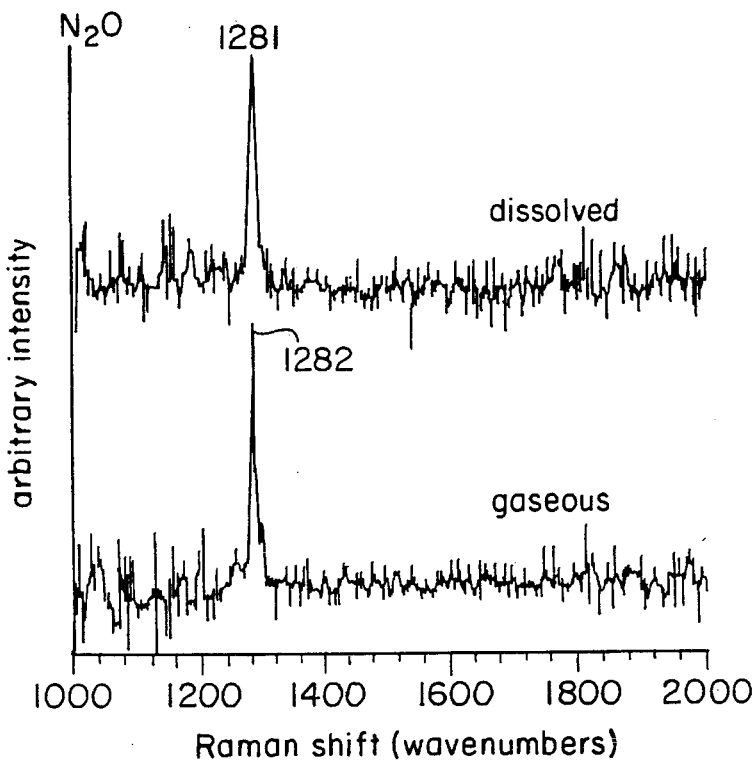
FIG. 7C graphically illustrates Raman background subtracted spectra of dissolved and gaseous $N_2O$ taken at 60 second integration.
Figure 7D:
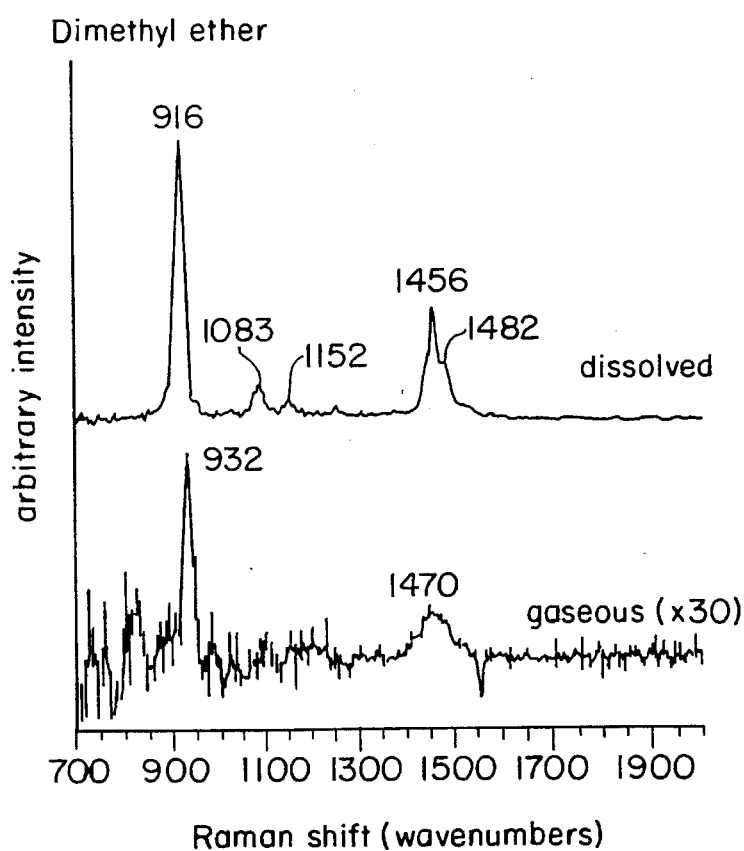
FIG. 7D graphically illustrates Raman background subtracted spectra of dissolved and gaseous dimethyl ether taken at 60 second integration for the dissolved and 10 minute integration for gas.
Figure 7E:
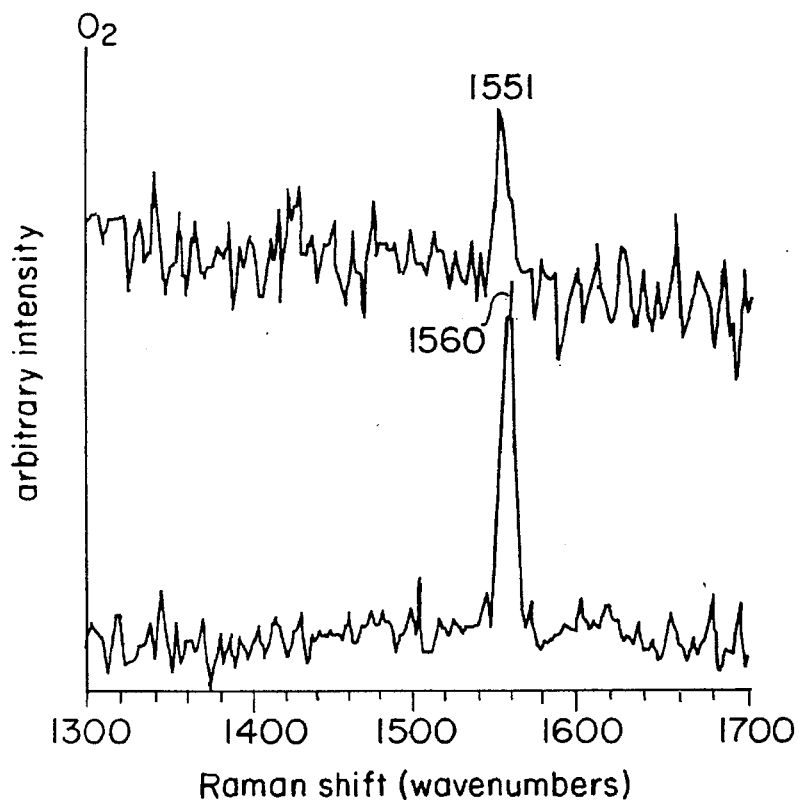
FIG. 7E graphically illustrates Raman background subtracted spectra of dissolved and gaseous $SO_2$ taken at 72 second integration for dissolved and 60 second for gas.

The Raman spectra of aqueous dissolved $CO_2$ and $O_2$ as shown in FIGS. 7A and 7E are the first reported measurements of such gases in dissolved aqueous state. The acquisition of these dissolved gas spectra particularly demonstrates the high level of sensitivity and reproducibility achievable by this embodiment of Raman spectroscopy method of the present invention.

Referring now to FIG. 7A, in the gaseous spectra of $CO_2$, the stretching band at 1388 $cm^{-1}$ slightly shifts to a lower frequency (1381 $cm^{-1}$) in the dissolved state. At the same time, the relative intensity of the bending overtone at 1286 $cm^{-1}$ strongly decreases. This is due to a strong shift in the bending mode of the dissolved state of $CO_2$ which results in an attenuation of the Fermi resonance.

Similarly, in the $O_2$ spectra shown in FIG. 7E, the stretching band shifts to lower energy by about 10 $cm^{-1}$. By contrast, the bands $SO_2$ and $N_2O$ shown in FIGS. 7B and 7C, respectively, did not shift noticeably in these spectra measurements.

In FIG. 7D, dimethyl ether displays the strongest changes between its Raman spectra in the dissolved and gaseous states. In addition to relatively large line shifts, "new" additional bands appear in the Raman spectrum of dissolved dimethyl ether at 1083 and 1152 $cm^{-1}$. The appearance of these two bands, which are seen in the IR spectrum of dimethyl ether in the gas phase, arise from a loss of symmetry in the dissolved state, due to a hydrogen bond between the central oxygen atom and a neighboring water molecule. This loss of symmetry relaxes the selection rules, allowing such IR-active modes to become Raman active as well.

The vibrational Raman lines from gases in the dissolved state show an increased line width compared to the corresponding gaseous state. This is generally due to faster vibrational relaxation of the gas molecules in the aqueous environment and also to an inhomogeneous broadening effect. However, in FIG. 7D, the rotational band in gaseous dimethyl ether around 1470 $cm^{-1}$ becomes more sharply defined in the dissolved phase; in fact, one can separately observe the symmetric and antisymmetric peaks.

Figure 8A:
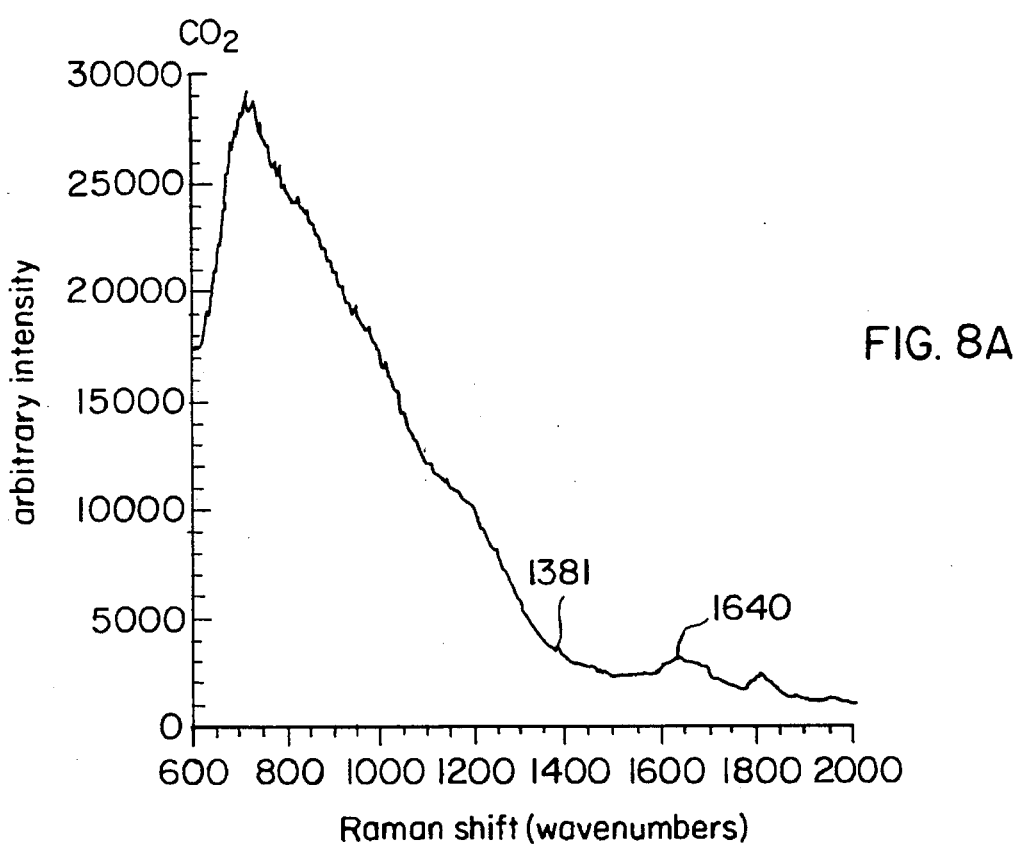
FIG. 8A graphically illustrates a spectrum of dissolved $CO_2$ in phosphate buffered saline (PBS), white-light corrected and without background subtracted. The location of the dissolved $CO_2$ peaks are notated (see FIG. 6A).

FIG. 8A graphically illustrates a typical white-light-corrected spectrum of a PBS sample, in this example, saturated with dissolved $CO_2$. Comparing the spectrum in FIG. 8A to the background-subtracted $CO_2$ spectrum in FIG. 7A indicates that the background dominates the overall spectrum even when the $CO_2$ is at its highest possible concentration. In fact, for most of the gases, the dissolved gas signal is small compared to the background Raman signal from PBS, the bottle, and the holographic filters.

As part of Raman spectral methods of the present invention, data from the gaseous samples collected as shown in FIGS. 7A to 7E are analyzed using a partial least square (PLS) method. PLS method is an efficient technique for extracting concentration predictions from multicomponent spectra. Optimal spectral range and bin size for PLS are then determined empirically by successive runs of the calculation. To verify the integrity of the prediction data, the dissolved gas concentration in liquid samples are measured on a commercial blood gas analyzer (Ciba Corning).

Figure 8B:
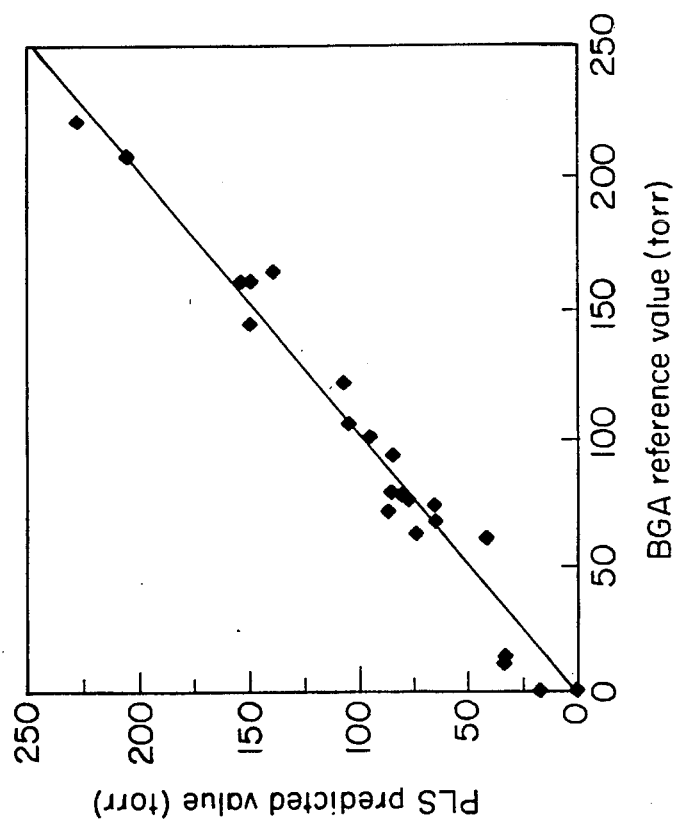
FIG. 8B graphically illustrates a PLS prediction of dissolved $CO_2$ concentration taken at 5 minute integration, where the solid line represents prediction and dots represent reference values taken from a gas analyzer. The uncertainty of prediction is 12 torr.

FIG. 8B graphically illustrates the comparison between the concentrations as predicted by the PLS cross-validation and the measured reference values by the blood gas analyzer. For this particular embodiment, electing the region from 1000 to 1500 $cm^{-1}$ and a bin size of 5 pixels, corresponding to a resolution of 15 $cm^{-1}$, gave the lowest prediction errors.

Such bin size corresponds roughly to the resolution of the particular embodiment of the system used and also to the typical natural line width of a Raman band in this regime. In FIG. 8B, the resulting root mean squared (RMS) error is 12 torr. The RMS error, however, is inversely proportional to the signal to noise (S/N) ratio. Therefore, doubling the S/N ratio reduces the RMS error by half. One way to reduce this error is by incorporating a more efficient collection geometry, such as the use of a CPC discussed above, to increase Raman signal collection.

Figure 9:
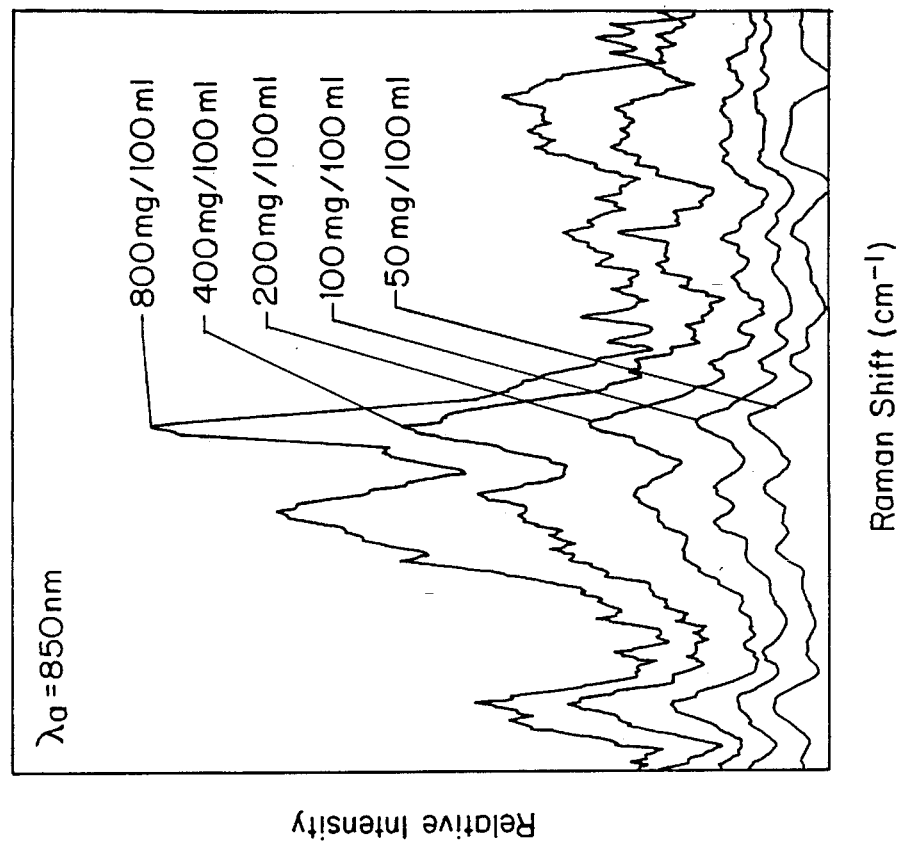
FIG. 9 graphically illustrates near infrared Raman spectra of glucose at various concentrations dissolved in saline.

In yet another preferred embodiment, methods of the present invention can be used to measure dissolved biological analytes such as glucose, lactic acid and creatinine. In particular, FIG. 9 graphically illustrates the NIR Raman spectra of glucose in saline at various concentrations in a line. The spectra were measured with 150 mW of 850 nm excitation light and the background contributions, mainly from water, were subtracted out. The spectral accumulation times are between 10 seconds for 8 mg/ml concentration and 5 minutes for 0.5 mg/ml concentration. The vibrational bands can be assigned to the skeleton mode of the glucose molecule. The spectra from lower concentration samples are processed with 7 point smoothing. The typical and normal physiological concentration of glucose in the blood stream of an adult is about 100 mg/100 ml. Hence, it is demonstrated here that sub-physiological concentration of glucose can be measured directly by NIR Raman spectroscopy system and methods of the present invention.

Figure 10B:
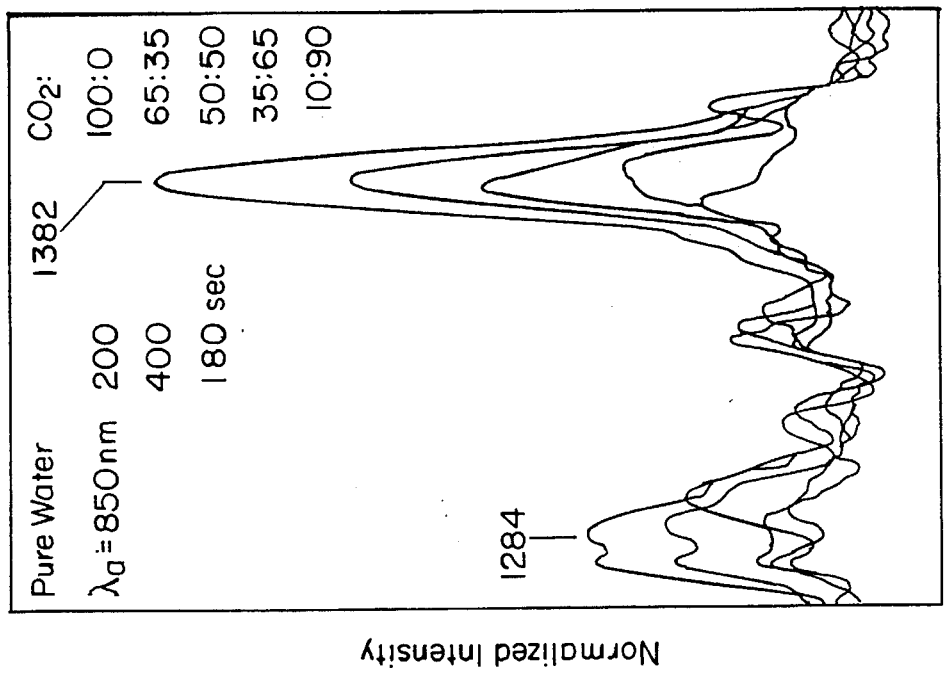
FIG. 10B graphically illustrates the same Raman spectra of $CO_2$ in FIG. 10A with background subtraction.
Figure 10A:
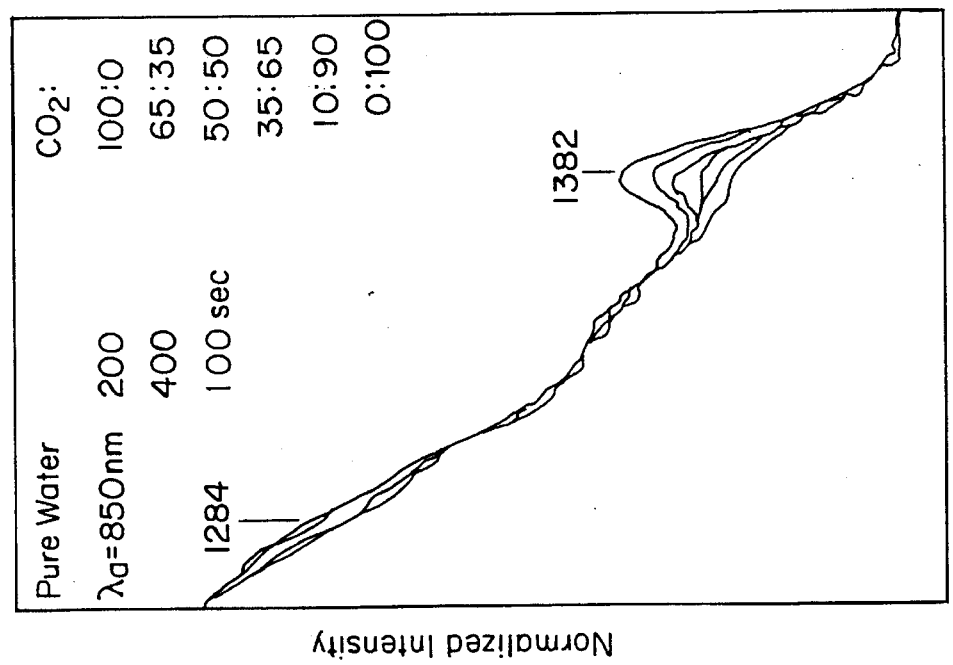
FIG. 10A graphically illustrates Raman spectra of carbon dioxide at various concentrations dissolved in saline without background substraction.

Again, the implementation of chemometric technique, such as the partial-least square (PLS) analysis discussed above, can be used to the extent that greater recovery of the spectral information, beyond the system resolution, is desired for accurate quantitative analysis. For example, FIGS. 10A and 10B show Raman spectra with and without background, respectively, of different amounts of $CO_2$ dissolved in saline. The Raman spectra were obtained with about 150 mW of 850 nm laser excitation in 3 minutes of spectral accumulation. One can see the contributions of the Raman bands associated with carbon dioxide (at 1284 $cm^{-1}$ and 1382 $cm^{-1}$). Note also that the presence of the noise can interfere with the interpretation of the Raman spectra in terms of both line shape and intensity, especially at dissolved gas concentrations lower than 30% of the full saturation level. The extent of interference is likely to increase with an increase in the complexity of the sample system.

FIG. 11 graphically illustrates the quality of a PLS analysis of the data presented in FIGS. 10A and 10B. Three loading vectors were used to generate the correlation between actual concentrations and the analytical concentrations. The correlation coefficient and its square are 0.9989 and 0.9978, respectively, representing a nearly perfect straight line through the coordinates (0,0) and (100, 100) points as shown in FIG. 11. Table 1 provides additional information on the PLS analysis.

TABLE 1

| Actual Concentration (Torr) | Analytical Concentration (Torr) | Difference (Torr) | Errors (%) |
|---|---|---|---|
| 0 | 0.707 | −0.707 | 0 |
| 76 | 77.801 | −1.801 | −2.370 |
| 266 | 252.160 | 13.840 | 5.200 |
| 380 | 384.469 | −4.469 | −1.176 |
| 494 | 500.566 | −6.566 | −1.329 |
| 760 | 746.799 | 13.201 | 1.737 |

As discussed above, chemometric methods such as the PLS technique, are a useful aspect of the present invention for extracting more accurate concentration levels of gases and analytes from Raman spectra. However, chemometric procedures are intricate, and many users treat them as "black boxes" that estimate concentrations with some empirically measured level of uncertainty. As part of the present invention, methods for analyzing given Raman spectra for extracting a sample concentration level include a numerical formula for measuring the level of uncertainty associated with a PLS analysis. In particular, a quantitative Raman data analysis involving PLS uncertainties on Raman data and includes the following steps.

First, Raman spectra of dissolved glucose, lactic acid, and creatinine (Sigma Chemical) in phosphate buffered saline (pH 7.4) are obtained by the system shown in FIG. 12A. These data are used as pure spectra in a computer to verify the uncertainty formula of the present invention. The Raman spectroscopy system for this analysis includes a excitation light source 312 which comprises a tunable dye laser 316 (Coherent 599) pumped by an argon-ion laser 314 (Spectra Physics Stabilite 2017). The excitation light of 830 nm at 200 mW is holographically filtered by a Kaiser filter 332 and then coupled into an f/1.7 100-micron-core silica optical fiber 320 (Corning). Light from the fiber is imaged 1:1 onto liquid samples held in a glass screw-top bottle 318 (1 cm diameter). Backscattered light from the sample is collected and re-imaged 1:1 into a seven-fiber probe 322 (6-around-1 geometry, see magnified view in FIG. 12B). At the proximal end of the probe, the fibers are redistributed into a column and coupled directly into the slit of a single-stage f/1.8 spectrograph 328 equipped with a holographic Raman edge filter 334 and a volume phase holographic transmission grating (Kaiser) optimized for a particular wavelength region as required by the sample. The grating disperses the collected light onto a 512 by 512 element, back-thinned, liquid nitrogen-cooled CCD chip 330 (Tektronix, Princeton Instruments). The CCD signal is binned vertically to create a single 512-pixel spectrum.

Figure 13:
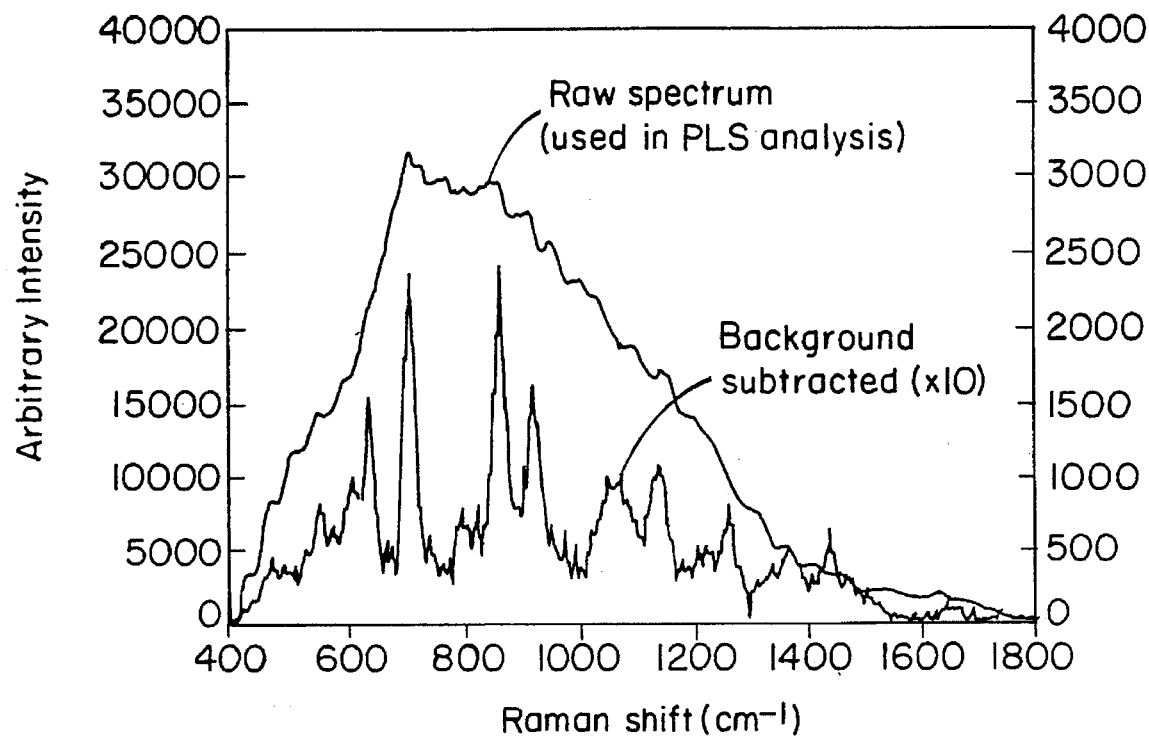
FIG. 13 graphically illustrates Raman spectrum of dissolved analyte mixture containing glucose, lactic acid, and creatinine in phosphate-buffered saline; integration time of 100 seconds.

FIG. 13 graphically illustrates a Raman spectrum of dissolved analyte mixture containing glucose, lactic acid, and creatinine in phosphate buffered saline, taken with the system in FIG. 12A for 100 seconds. The mixture sample was prepared from 100 mM stock solutions of glucose, lactic acid, and creatinine in phosphate-buffered saline solution (pH 7.4). In the mixture, molarities of individual analytes ranged from 0 to 100 mM. FIG. 13 shows the mixture spectrum with and without subtraction of the background from the system and saline. Note that the Raman bands from the analytes are seen to be small compared to the overall signal.

Figure 14A:
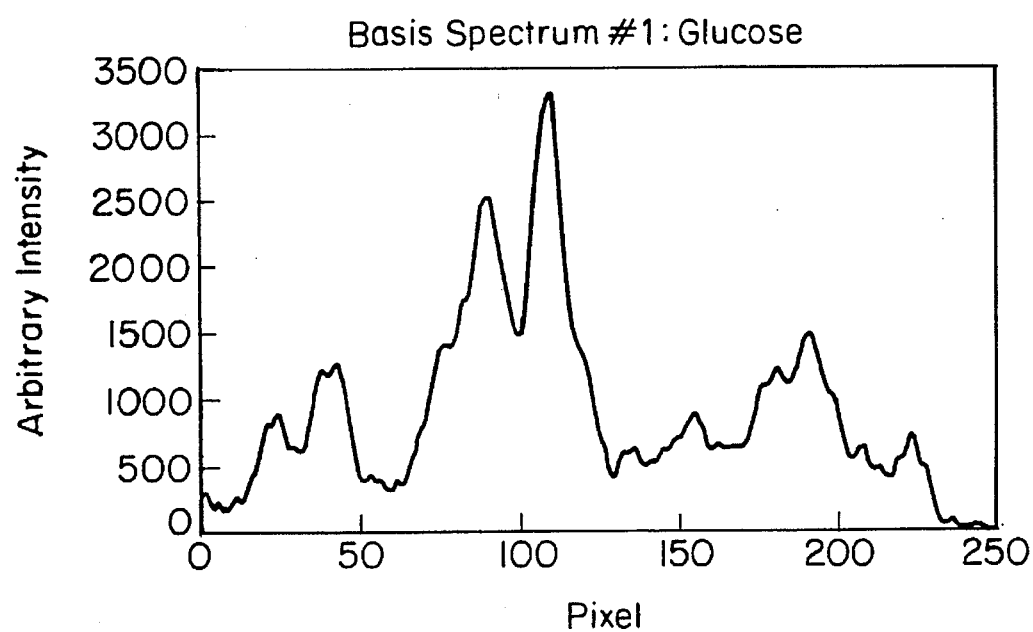
FIGS. 14A to 14C graphically illustrate pure, smoothed spectra for the same analytes, as shown mixed in FIG. 13, glucose, lactic acid, and creatinine, respectively.
Figure 14B:
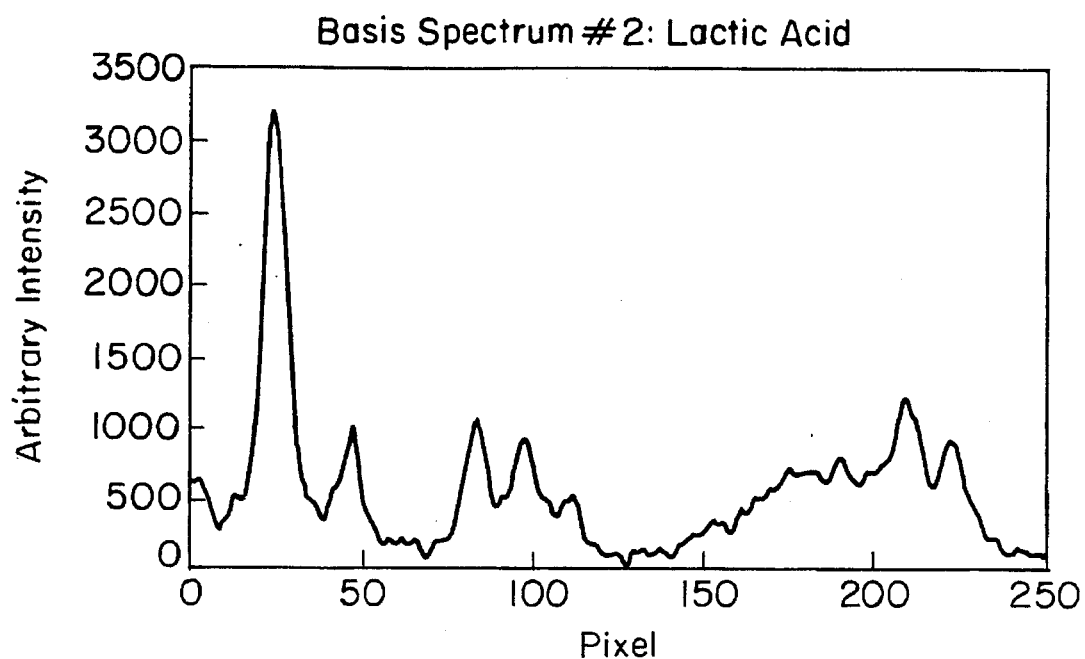
Figure 14C:
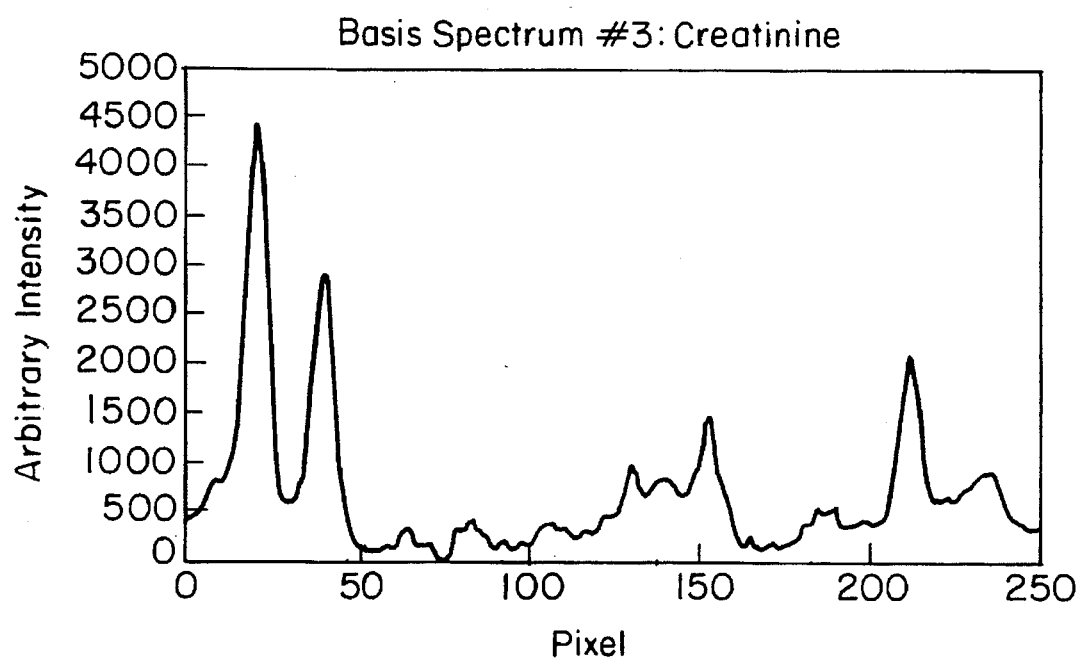

Second, spectra are saline-background subtracted and then smoothed to produce three "pure" analyte spectra. These spectra are shown in FIGS. 14A to 14C. A spectra set is needed for calibration and consists of twenty random combinations of these three pure spectra. A PLS calibration is performed separately for glucose, lactic acid, and creatinine, using the known concentrations as references. In each case, three weight vectors (w), loading vectors (b), and score coefficients (v) are generated for use in the uncertainty formula. From these an equation for computing the average (RMS) concentration uncertainty, e, can be written as:

$$\bar{e} = \bar{n} \sqrt{\sum_{i=1}^{m} \psi_i^2}$$

where

-continued $$\psi_1 - v_i + \sum_{j=i+1}^{m} (-1)^{j-1} \left( \prod_{k=1}^{j-1} b_{j-k}v_{k+1}^+ \right) v_j$$

where $\bar{n}$ is RMS noise amplitude. Here the vectors are models underlying pure spectra, and the coefficients are indications of how much information about the desired analyte resides in each vector.

Figure 15:
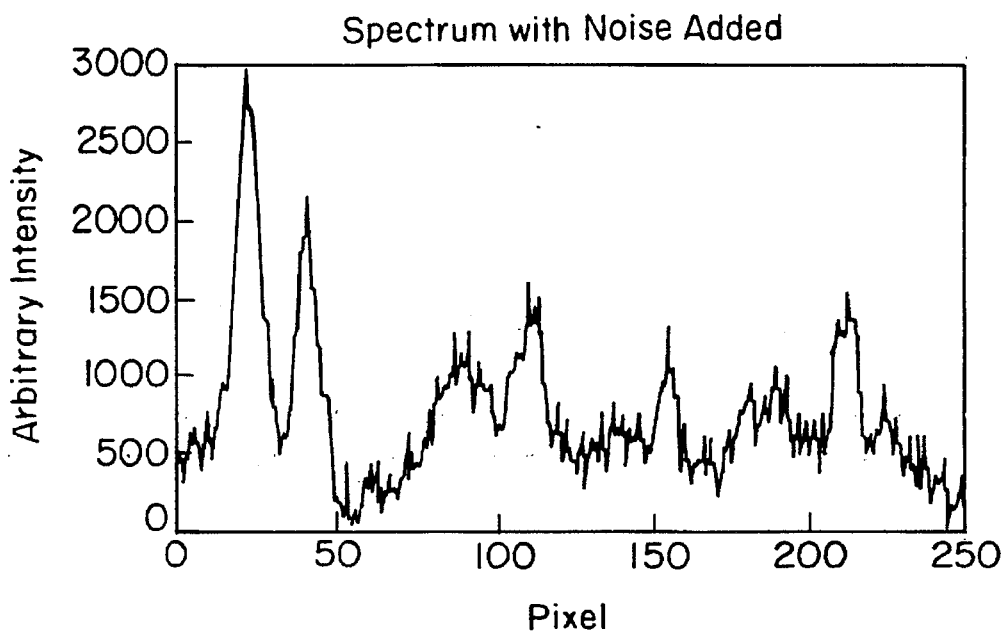
FIG. 15 graphically illustrates a typical mixture of the pure spectra in FIGS. 14A to 14C, with noise added.

Third, simulated noise with a mean value of zero and a known RMS value is added to a set of unknown spectra or a "prediction set" consisting of another twenty random combinations of the pure spectra. A typical mixture spectrum with noise is shown in FIG. 15.

Finally, a PLS analysis of the three analytes is then performed on the twenty unknown spectra, using the calibration from the noiseless training set. The RMS error for each analyte is calculated.

Figure 16A:
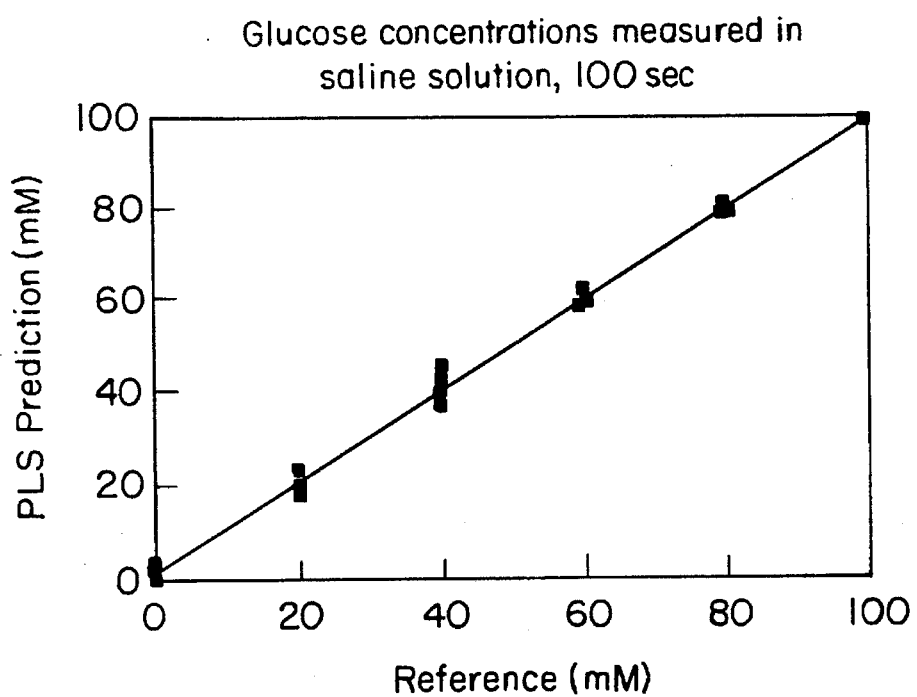
FIGS. 16A and 16B graphically illustrate PLS predictions of glucose and creatinine, respectively, versus reference values taken by 100 second Raman spectra; the RMS prediction error for glucose is 1.9 mM and 1.5 mM for creatinine.
Figure 16B:
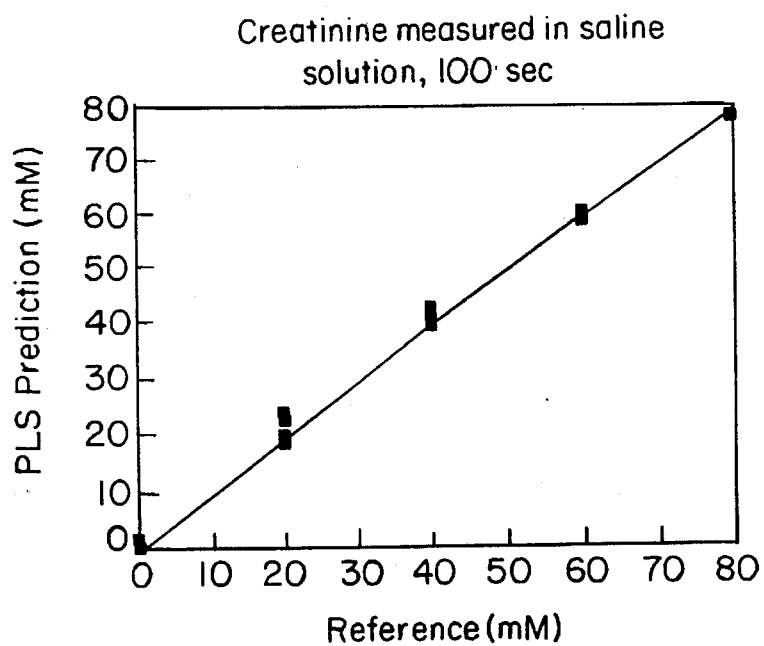

The uncertainties from the computer are shown in part in FIGS. 16A and 16B and listed more completely in Table 2 below, along with the analytically calculated values. For all three analytes, uncertainties from the calculation are consistent with those determined by the theoretical calculations of equation (1).

TABLE 2

| Analyte | Theory | Simulation | Simulation/Theory |
|---|---|---|---|
| Glucose | .00890 | .00925 | 1.03 |
| Lactic acid | .0153 | .0169 | 1.10 |
| Creatinine | .00975 | .00960 | 0.98 |

Table 1. Results from PLS analysis of computer-simulated Raman.

The uncertainties from the experimental data are compiled in Table 3 below, along with the calculated minimum uncertainties. In the 100 second spectra of the actual data, no more than 2.1 mM (for lactic acid) of RMS error of analysis is observed. The RMS errors of for glucose and creatinine define acceptable parameters at 1.9 mM and 1.5 mM, respectively, and are shown in FIGS. 16A and 16B. This method of analysis provides a process for examining collected data and determining whether it falls within appropriate limits and thus used for further diagnostic analysis.

TABLE 3

| | Glucose | Lactic acid | Creatinine |
|---|---|---|---|
| 20-second spectra: | | | |
| Minimum PLS uncertainty (from theory) | 2.1 mmol/L | 2.9 mmol/L | 1.9 mmol/L |
| Experimental PLS uncertainty | 2.9" | 3.6" | 2.6" |
| % above estimated minimum | 38% | 24% | 37% |
| 100-second spectra: | | | |
| Minimum PLS uncertainty (from theory) | 0.9 mmol/L | 1.3 mmol/L | 0.8 mmol/L |
| Experimental PLS uncertainty | 1.9" | 2.1" | 1.5" |
| % above theoretical minimum | 111% | 65% | 74% |

Known levels of analytes were added to cuvettes of human whole blood, the samples were scanned on a Raman system as illustrated in herein, in this particular example for a collection time of five minutes, and a PLS process was used to extract concentrations. In order to use the data efficiently, a cross-calibration was performed in which one sample at a time is rotated out of the calibration set and analyzed.

Figure 17A:
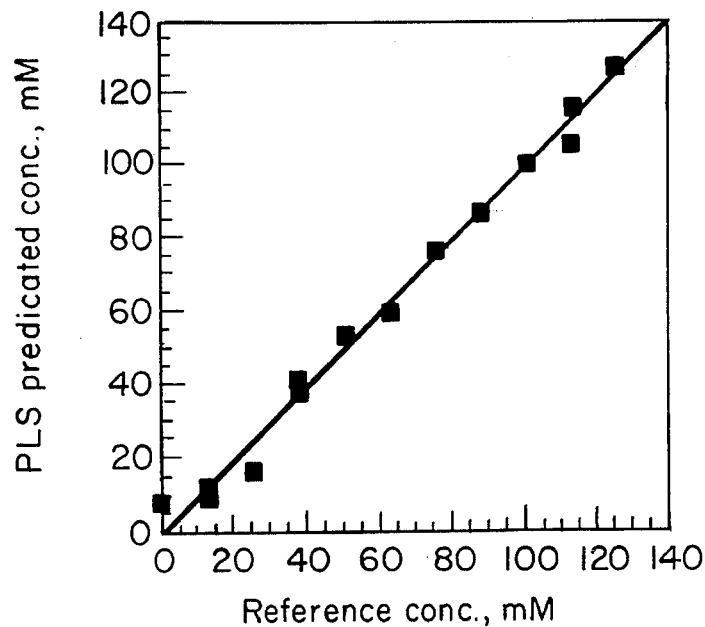
FIGS. 17A and 17B graphically illustrate measurements in human whole blood.
Figure 17B:
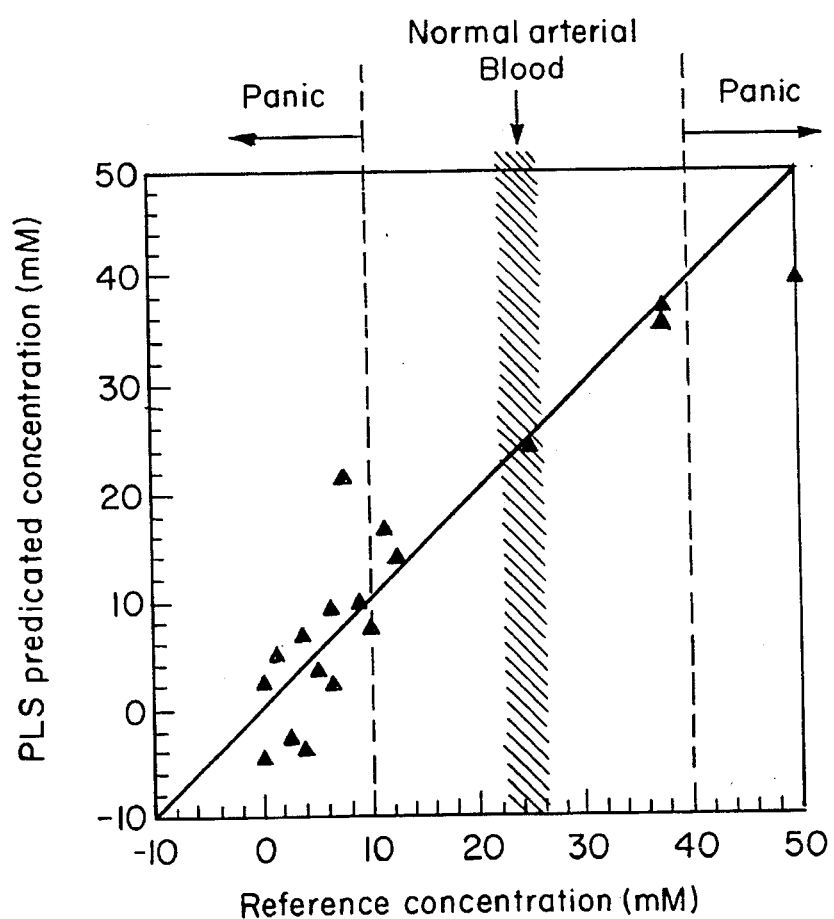

FIG. 17A shows PLS cross-calibration results for glucose in human whole blood, and FIG. 17B shows PLS results for bicarbonate in human whole blood. The results for analysis of glucose in whole blood had an average uncertainty=4.0 mM. The power delivered to the whole blood was 150 mW and the number of collection fibers in this example was one. The collection time can be reduced and accuracy of the measurement can be increased by using a CPC and additional fibers.

The results for bicarbonate in whole blood had an average prediction uncertainty=5.0 mM. Experimental parameters are the same as for glucose. The shaded region in FIG. 17B indicates the range of typical levels of bicarbonate in human whole blood; dashed lines indicate high and low levels that are important to discriminate in a clinical setting.

Figure 18:
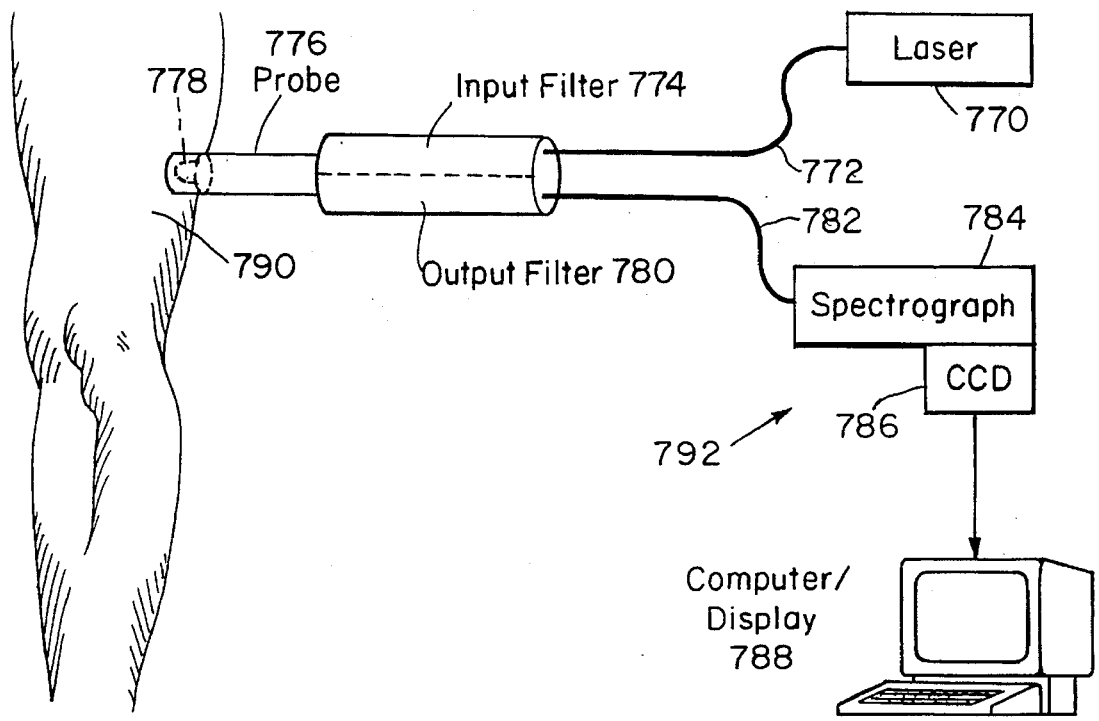
FIG. 18 is a schematic illustration of a hand held probe for transdermal blood measurement.
Figure 19:
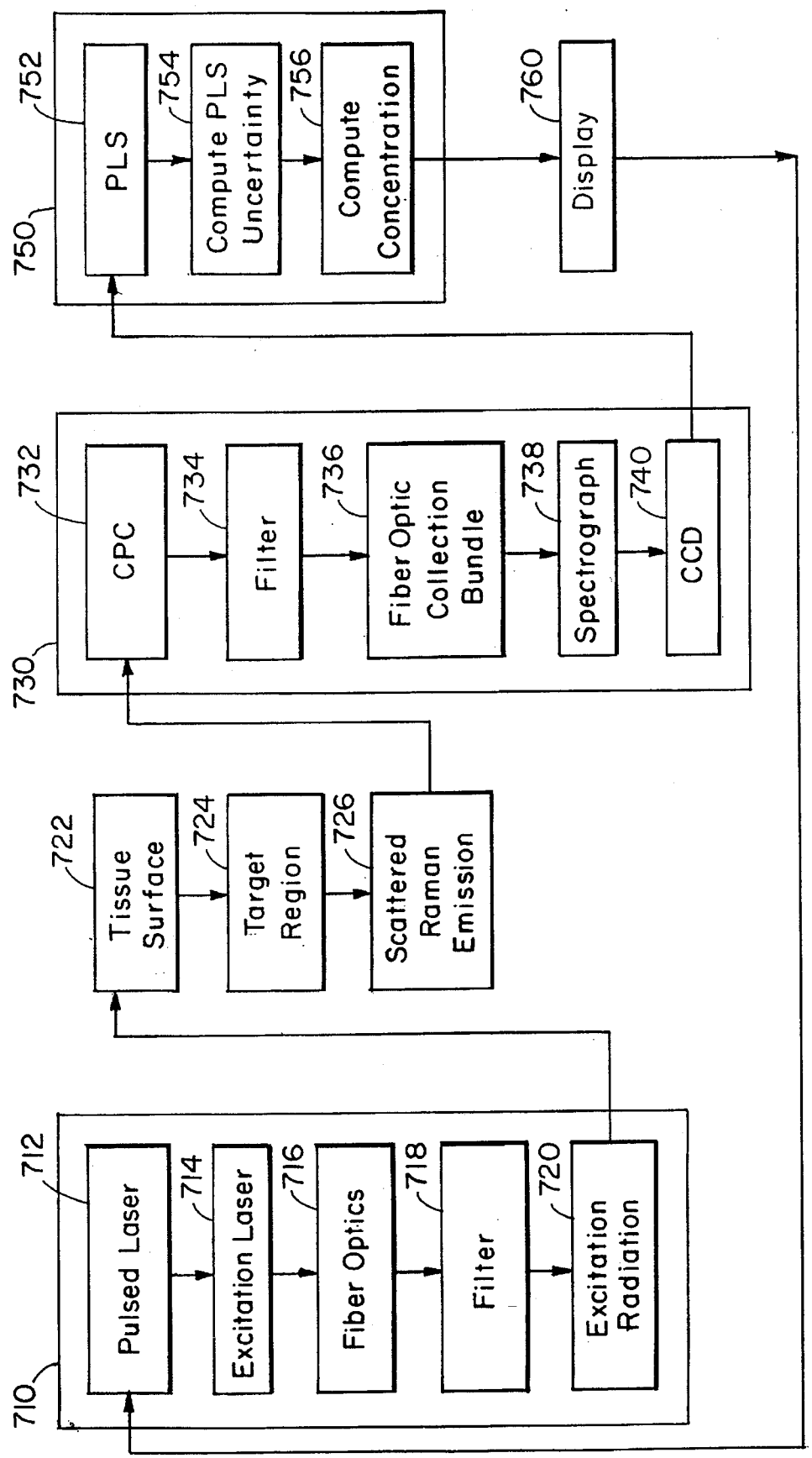
FIG. 19 is a flow chart describing a continuous transdermal spectroscopic measurement in accordance with the present invention.

A system for performing continuous transdermal monitoring of a patients blood is illustrated in FIG. 18. A flowchart in FIG. 19 illustrates a preferred method of using the system of FIG. 18. This particular sequence of steps describes continuous transdermal monitoring and analysis of a blood region below a portion of a human skin surface by a Raman spectroscopy system in accordance with the methods and systems of the present invention. The system portion of this particular embodiment can be divided into three major subsystems: excitation step 710, Raman collection/detection step 730, and data analysis step 750. The excitation phase comprises a pulsed laser source 712 for providing a range of excitation laser pulses 714, a fiber optic carrier 716 coupled to the laser source, and a holographic input filter 718 for removing any fiber background and producing a filtered excitation laser 720. A blood region 724 below a portion of skin surface 722 is then irradiated by the filtered laser. The target blood region scatters the incident light to produce a Raman scattered signal 726.

The filters and distal end of the probe provide a hand-held unit which can use either an optical shield, lens or CPC on the distal end to provide optical coupling to the tissue.

In the collection/detection phase in the method of FIG. 19, scattered Raman light is collected by a CPC 732 and filtered by a holographic output filter 734, which is coupled to the proximal end of the CPC. Such collected and filtered Raman light is then transmitted by a fiber optic collection bundle 736 having appropriate numerical aperture that matches the output diameter of the CPC. The output end of the fiber optic bundle is coupled to a detection system consisting of a spectrograph 738 and a CCD 740. High resolution reading of the filtered Raman data is then performed by the combined subsystem of spectrograph and CCD.

In the data analysis phase, the sampled Raman data is analyzed and categorized by using a PLS technique 752. The results are then checked for error arising from various uncertainties 754. Finally, the concentration level for a particular sample of blood being analyzed is computed 756. A display monitoring system 760 displays the concentration levels of various blood analytes and gases determined by the above-described methods and runs such diagnosis continuously by periodically triggering the laser source to generate excitation laser pulses.

An apparatus which may be used for carrying out the analysis process of FIG. 18 is shown in FIG. 19. A laser source 770 generates a continuous wave, or a chain of excitation laser pulses at a fixed frequency. An optical fiber carrier 772 is coupled to the laser source and delivers the excitation laser to an optical filter 774. The filtered excitation laser is then focused to irradiate a blood region below a portion of tissue surface 790 through a probe 776. Raman-scattered light emitted in response to the excitation laser is collected by a CPC 778 at the distal end of the probe. The collection of Raman light is filtered by an output filter 780 and delivered to a detection system 792 comprised of a spectrograph 784 and a CCD 786 by an optical fiber carrier 782. An analysis system comprising a computer/display 788 coupled to the detection system processes raw data from the detection system to determine concentrations of dissolved blood gases and analytes in the target blood region.

Figure 20:
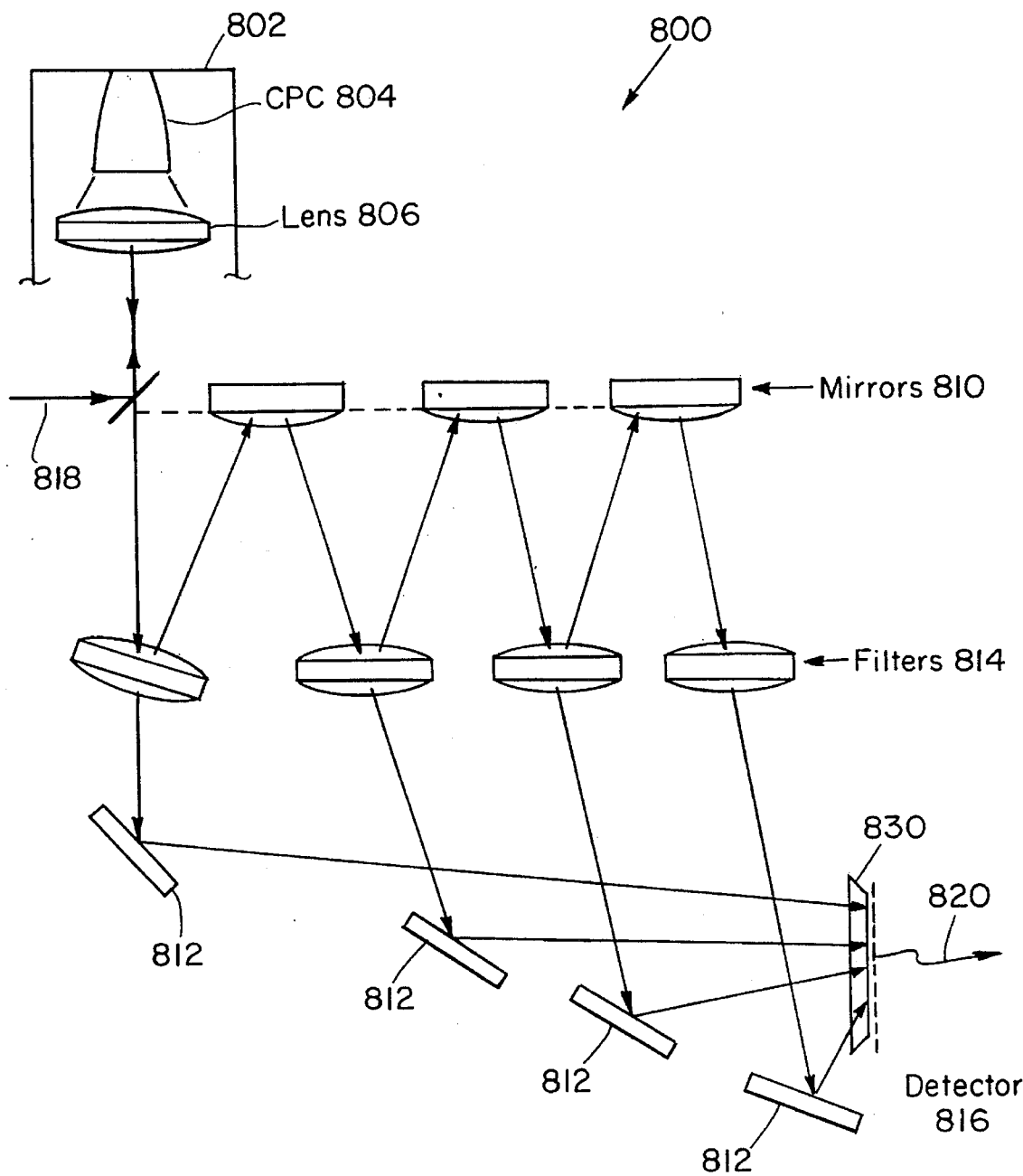
FIG. 20 is an enlarged illustration of a hand-held probe in accordance with the invention utilizing interference filters.

FIG. 20 illustrates in schematic form a hand-held diagnostic probe 800 including a distal end 802 through which light is delivered and collected, the distal end can house a CPC 804 and lens 806. The distal end can also include a number of miniature CPCs in an array and, with fiber optics, is used along with the appropriate lens to provide an imaging capability in this or other embodiments described herein. In this embodiment, however, a plurality of mirrors 810, 812 and interference filters 814 are used to deliver plurality of frequencies of light directly onto a detector. In this particular example, four frequencies are detected by detector 816 and the resulting data are delivered by cable 820 to a computer for analysis. Light 818 from the laser source is coupled to the CPC between the lens 806 and the interference filters. This system illustrates, in particular, a collection geometry without optical fibers. Additionally, another CPC 830 can also be used with this and other embodiments described herein to deliver collected light onto the detector where the small aperture of the CPC is coupled to the detector surface.

Equivalents

While the invention has been described in connection with specific methods and apparatus, it is to be understood that the description is by way of example and not as a limitation to the scope of the invention as set forth in the claims.

The invention claimed is:

1. A method of measuring a dissolved gas in blood comprising the steps of:
    irradiating blood with laser radiation having a wavelength such that Raman scattering occurs in a dissolved gas in the irradiated blood;
    collecting Raman scattered light from the dissolved gas; and
    detecting the collected Raman-scattered light from the dissolved gas in response to the laser radiation.

2. The method of claim 1 further comprising determining a concentration of the dissolved gas in the blood.

3. The method of claim 2 further comprising determining the concentration of a dissolved gas selected from the group comprising $O_2$, and $CO_2$.

4. The method of claim 1 wherein the laser wavelength is within the range of 700–1000 nm.

5. The method of claim 1 further comprising generating a spectral representation from the detected light and analyzing the spectral representation to measure a plurality of blood analytes.

6. The method of claim 1 further comprising providing an optical collimator on the distal end of a fiber optic device and collecting the Raman scattered light through the optical collimator.

7. The method of claim 1 further comprising providing a fiber optic probe coupled to a laser and irradiating said blood with radiation through the fiber optic probe.

8. The method of claim 1 further comprising providing a fiber optic collector for collecting the Raman scattered light.

9. The method of claim 8 further comprising providing a first optical filter between a laser source of the radiation and the irradiated blood and providing a second optical filter between the irradiated blood and the fiber optic collector.

10. A method of spectroscopic analysis of blood comprising the steps of:
    transdermally irradiating blood through a portion of tissue with laser radiation having an excitation wavelength; and
    detecting Raman-scattered light from the blood in response to the laser radiation, the Raman-scattered light having a wavelength different from the excitation wavelength of the laser radiation.

11. The method of claim 10 further comprising coupling the laser radiation to the tissue with a first fiber optic device and collecting the Raman-scattered light with a second fiber optic device, the second fiber optic device being coupled to a detector which detects the Raman-scattered light.

12. The method of claim 11 further comprising filtering the laser radiation with a first optical filtering device and filtering the Raman-scattered light with a second optical filtering device to remove any background light including Raman-scattered light produced by the first fiber optic device or the second fiber optic device.

13. The method of claim 10 further comprising analyzing the Raman-scattered light to extract concentration levels of blood gases and analytes in the blood.

14. The method of claim 10 further comprising irradiating the blood with radiation having a wavelength in a range of 700–1000 nm.

15. The method of claim 10 further comprising detecting dissolved blood gases and an electrolyte in the blood.

16. The method of claim 15 wherein the step of detecting blood gasses further comprises detecting a dissolved blood gas selected from the group comprising $O_2$ and $CO_2$.

17. The method of claim 10 further comprising providing an optical concentrator for collecting Raman scattered light from the blood, the collected light being optically coupled to a detector.

18. A method of spectroscopically monitoring blood comprising the steps of:
    positioning a probe in proximity to a lumen containing the blood of a patient;
    periodically irradiating a region of the blood within the lumen with laser radiation having an excitation wavelength; and
    detecting Raman-scattered light from the blood in response to the periodic laser radiation, the Raman-scattered light having a wavelength different from the wavelength of the excitation laser radiation.

19. The method of claim 18 further comprising coupling the laser radiation to tissue overlying the blood with a first fiber optic device and collecting the Raman-scattered light with a second fiber optic device, the second fiber optic device being coupled to a detector which detects the Raman-scattered light.

20. The method of claim 18 further comprising filtering the laser radiation pulses with a first optical filtering device and filtering the Raman-scattered light with a second optical filtering device to remove any background light including Raman-scattered light produced by the first fiber optic device or the second fiber optic device.

21. The method of claim 18 further comprising analyzing the Raman-scattered light to extract concentration levels of blood gases and analytes in the blood region.

22. A method of spectroscopic analysis of blood comprising the steps of:

irradiating a dissolved gas in blood with laser radiation;

detecting a spectrum of Raman-scattered light returning from the dissolved gas in response to the laser radiation, the Raman-scattered light having a plurality of wavelengths different from the wavelength of the excitation laser radiation; and subtracting a background spectrum from the detected spectrum.

23. The method of claim 22 further comprising coupling the laser radiation to the sample with a first fiber optic device and collecting the Raman-scattered light with a second fiber optic device, the second fiber optic device being coupled to a detector which detects the Raman-scattered light.

24. The method of claim 23 further comprising filtering the laser radiation with a first optical filtering device and filtering the Raman-scattered light with a second optical filtering device to remove any background light including Raman-scattered light produced by the first fiber optic device or the second fiber optic device.

25. The method of claim 22 further comprising analyzing the Raman-scattered light to determine concentration levels of blood gases and analytes in the sample.

26. The method of claim 22 further comprising providing a diode laser for irradiating the blood.

27. A transdermal spectroscopic diagnostic system for analyzing human blood comprising:

a laser emitting radiation in the infrared spectrum at a wavelength to penetrate a layer of tissue;

a fiber optic device optically coupled to the laser for delivering the infrared radiation through the layer of tissue to irradiate a region of blood underlying the tissue;

a first optical filter having an input end coupled to a distal end of the fiber optic device that filters light, and an output end for passing the laser radiation;

an optical concentrator which comprises a cavity that reflects light and an aperture at a distal end that collects light, including the Raman-scattered light from blood over a range of incident angles, and an output path at the proximal end having a diameter larger than that of the aperture for transmitting collected light, coupled to the output end of the first filter;

a fiber optic bundle having an input end coupled to a second optical filter for passing the Raman-scattered light and an output end for delivering the Raman-scattered light, and a detector coupled to the output end of the fiber optic bundle for detecting the Raman-scattered light; and a data processor that determines a concentration level of an analyte in blood.

28. Amended The system of claim 27, wherein the detector comprises:

a first subsystem comprising a spectrograph coupled to a charge-coupled-device for detecting the Raman-scattered light, and a second subsystem comprising an analyzer that determines a concentration level of a dissolved blood gas or analyte from the detected Raman-scattered light.

29. The system of claim 27, wherein the first filter comprises a holographic bandpass filter and further comprising a holographic dichroic beamsplitter.

30. The system of claim 27, wherein the optical concentrator comprises a compound parabolic concentrator.

31. The system of claim 27, wherein the fiber optic bundle comprises an aperture at the input end that is approximately equal in dimension to the diameter of the output path of the concentrator, and the output end having fiber optic strands configured in a plurality of vertical columns corresponding to the resolution of the detector.

32. A method of measuring a dissolved gas in blood comprising the steps of:

irradiating blood with laser radiation having a wavelength in the range of 700 to 1300 nm such that Raman scattering occurs in a dissolved gas in the irradiated blood;

collecting Raman scattered light from the dissolved gas; and detecting the collected Raman-scattered light from the dissolved gas in response to the laser radiation.

33. The method of claim 32 further comprising determining a concentration of the dissolved gas in the blood.

34. The method of claim 33 further comprising determining the concentration of a dissolved gas selected from the group comprising $O_2$, and $CO_2$.

35. The method of claim 32 wherein the laser wavelength is within the range of 800–1000 nm.

36. The method of claim 32 further comprising generating a spectral representation from the detected light and analyzing the spectral representation to measure a plurality of blood analytes.

37. The method of claim 32 further comprising providing an optical collimator on the distal end of a fiber optic device and collecting the Raman scattered light through the optical collimator.

38. The method of claim 32 further comprising providing a fiber optic probe coupled to a laser and irradiating said blood with radiation through the fiber optic probe and collecting the Raman-scattered light.

* * * * *